US008688459B2

(12) United States Patent
Nenov et al.

(10) Patent No.: US 8,688,459 B2
(45) Date of Patent: Apr. 1, 2014

(54) VOICE-CONTROLLED CLINICAL INFORMATION DASHBOARD

(75) Inventors: Valeriy I. Nenov, Los Angeles, CA (US); Neil A. Martin, Encino, CA (US); Farzad D. Buxey, Marina del Rey, CA (US); Xiao Hu, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 939 days.

(21) Appl. No.: 12/247,981

(22) Filed: Oct. 8, 2008

(65) Prior Publication Data

US 2009/0177477 A1 Jul. 9, 2009

Related U.S. Application Data

(60) Provisional application No. 60/978,395, filed on Oct. 8, 2007.

(51) Int. Cl.
*G10L 21/00* (2013.01)
*G10L 15/26* (2006.01)
*G10L 15/18* (2013.01)
*G06F 19/00* (2011.01)
*A61B 17/00* (2006.01)

(52) U.S. Cl.
CPC ........... *G10L 15/265* (2013.01); *G10L 15/1815* (2013.01); *G06F 19/322* (2013.01); *G06F 19/3406* (2013.01); *A61B 2017/00203* (2013.01)
USPC ........................................ 704/275

(58) Field of Classification Search
CPC . G10L 15/265; G10L 15/1815; G06F 19/322; G06F 19/3406; A61B 2017/00203
USPC ................ 340/12.54; 704/270, 251, 275
See application file for complete search history.

(56) References Cited

U.S. PATENT DOCUMENTS

| 5,335,313 | A  | * | 8/1994 | Douglas ........................ 704/275 |
| 5,920,836 | A  | * | 7/1999 | Gould et al. .................. 704/251 |
| 6,014,626 | A  | * | 1/2000 | Cohen ........................... 704/275 |
| 6,233,559 | B1 | * | 5/2001 | Balakrishnan ................ 704/275 |
| 6,278,975 | B1 | * | 8/2001 | Brant et al. ................... 704/275 |
| 6,446,001 | B1 | * | 9/2002 | Sakai et al. ................... 701/439 |
| 6,762,692 | B1 | * | 7/2004 | Mingot et al. ............. 340/12.54 |
| 6,944,536 | B2 | * | 9/2005 | Singleton ...................... 701/410 |
| 7,027,808 | B2 | * | 4/2006 | Wesby ........................... 455/419 |
| 7,099,825 | B1 | * | 8/2006 | Cook ............................. 704/251 |

(Continued)

FOREIGN PATENT DOCUMENTS

EP 0681284 A2 11/1995

OTHER PUBLICATIONS

What Matters i suite(TM); "A Family if Integrated Surgical Suites Customized for Your Environment" NavSuite Operating Room; Stryker 2004-2009; 3 pages.

(Continued)

*Primary Examiner* — Michael Colucci
(74) *Attorney, Agent, or Firm* — St. Onge Steward Johnston & Reens LLC

(57) ABSTRACT

A method provides a display area of a computer system for displaying a set of data. The data includes clinical data for one or more medical patients. The method provides multiple controls for performing multiple functions. The method provides an audio interface for controlling at least one of the controls through audio commands.

37 Claims, 22 Drawing Sheets

(56) References Cited

U.S. PATENT DOCUMENTS

| | | | |
|---|---|---|---|
| 7,259,906 B1* | 8/2007 | Islam | 359/334 |
| 7,426,467 B2* | 9/2008 | Nashida et al. | 704/275 |
| 8,015,014 B2* | 9/2011 | Wang et al. | 704/275 |
| 2002/0194029 A1* | 12/2002 | Guan et al. | 705/3 |
| 2003/0033312 A1* | 2/2003 | Koizumi et al. | 707/100 |
| 2003/0139933 A1 | 7/2003 | Kimmel | |
| 2003/0220819 A1* | 11/2003 | Burstein et al. | 705/3 |
| 2004/0193413 A1* | 9/2004 | Wilson et al. | 704/243 |
| 2004/0210442 A1* | 10/2004 | Glynn et al. | 704/275 |
| 2005/0033223 A1* | 2/2005 | Herrera | 604/67 |
| 2005/0055215 A1* | 3/2005 | Klotz | 704/275 |
| 2005/0114140 A1* | 5/2005 | Brackett et al. | 704/270 |
| 2005/0222933 A1* | 10/2005 | Wesby | 705/36 |
| 2005/0277872 A1* | 12/2005 | Colby et al. | 604/67 |
| 2006/0149558 A1* | 7/2006 | Kahn et al. | 704/278 |
| 2006/0281989 A1* | 12/2006 | Viswanathan et al. | 600/424 |
| 2007/0080801 A1* | 4/2007 | Weismiller et al. | 340/539.13 |
| 2007/0083395 A1 | 4/2007 | Fors et al. | |
| 2007/0166690 A1* | 7/2007 | Johnson | 434/365 |
| 2008/0037720 A1* | 2/2008 | Thomson et al. | 379/88.01 |
| 2008/0037727 A1* | 2/2008 | Sivertsen et al. | 379/88.13 |
| 2008/0208630 A1* | 8/2008 | Fors et al. | 705/3 |

OTHER PUBLICATIONS

Versweyveld; "Abbott Northwestern Installs Fully-Inegrated, Voice-Controlled Operating Room of the Future"; Virtual Medical Worlds Monthly; Aug. 7, 2002; 2 pages.

Windyga, et al.; "Augmented Vision for Minimally Invasive Abdominal Cancer Surgery"; Proceedings of the 25th Annual International Conference of the IEEE EMBS; Sep. 2003; 4 pages.

Smallcapreview.com; "Computer Motion (Nasdaq-RBOT)"; 1999-2004 SmallCapReview.com. Contact info: editor@smallcaprerview.com; 10 pages.

Metzger; "Digital Control System Delivers Operating Room Interface"; ThomasNet Industrial NewsRoom; Smith & Nephew Dyonics, Inc.; Apr. 12, 2006; 5 pages.

C.A.R.E. Care Area Reports and Essentials; "Effectively Improving Patient Safety"; 2006; 3 pages.

Nathan, et al. "The Voice-Controlled Robotic Assist Scope Holder AESOP for the Endoscopic Approach to the Sella"; Skull Base: An Interdisciplinary Approach; Aug. 2006; 9 pages.

Salama, et al.; "Utility of a Voice-Activated System in Minimally Invasive Surgery"; Journal of Laparoendoscopic & Advanced Surgical Techniques, vol. 15, No. 5; 2005; 4 pages.

Guerrouad; "Voice Control in the Surgery Room"; Engineering in Medicine and Biology Society, 1989. Images of the Twenty-First Century., Proceedings of the Annual International Conference of the IEEE Engineering in pp. 904-905 vol. 3 Nov. 9-12, 1989.

Martine Kempf; "Voice-Control Used in Microsurgery Since 1984"; Kempf Katalavox; Contact Info: webmaster@katalavox.com; 1995-2002 Martine kmepf; 1 page.

Canadian Office Action, Application No. 2,702,079, Issued: Aug. 21, 2013, 4 pages.

* cited by examiner

VOICE-CONTROLLED CLINICAL INFORMATION DASHBOARD

CLAIM OF BENEFIT TO PRIOR APPLICATION

This application claims the benefit of the earlier filed U.S. Provisional Patent Application No. 60/978,395, entitled "Voice Controlled Clinical Information Dashboard," filed on Oct. 8, 2007. This Provisional Patent Application, namely Provisional Patent Application No. 60/978,395, is herein incorporated by reference.

FIELD OF THE INVENTION

The invention relates to systems and methods for manipulating display information, such as clinical information used in providing medical services, using auditory commands.

BACKGROUND OF THE INVENTION

As more industries and service providers become more information reliant, a need exists to manage and access the accumulated information in an efficient and uncomplicated manner. As a result, database management systems have been established to store and track the prolific amounts of data associated with any enterprise or small scale business. Specifically, in hospitals, health care organizations, and the medical field in general, the digitization of patient information has resulted in specialized databases that allow different medical practitioners to contribute to a single digital copy of the patient file irrespective of the location of the medical practitioner. For instance, because of digitization of information, a surgeon may gain access to information regarding the patient's vitals that were entered by a nurse the previous evening.

Additionally, such digitization of patient information has successfully allowed medical practitioners to carry medical history and patient information of some or all their patients in portable electronic devices such as personal digital assistants ("PDAs"), laptop computers, or remote terminal clients. Alternatively, patient information may be wirelessly transmitted to medical practitioners' electronic devices. Digital data further allows medical practitioners to quickly share information with other medical practitioners for various purposes via electronic data transmission, such as email. Medical practitioners are now, more than ever, able to readily obtain patient information quickly and securely.

However, acquiring such information often presents various challenges due to the fact that different devices each have their own proprietary means of data representation, encapsulation, and storage. Often, the data gathering systems are provided by different vendors, and each one requires separate user login procedures and provides different navigable interfaces. For example, a heart rate monitor may create and store a graphical representation of a patient's heart rate over a period of time, and a blood pressure monitor may create and store numeric values for the patient's blood pressure over the same period of time. Therefore, the data from one device may not be readable by another device. Similarly, the data from one device may not be stored within the same database as the data of another device without first performing some form of data conversion or data manipulation.

Furthermore, a medical practitioner often must use a manual input device (e.g., a mouse, keyboard, etc.) of a computer to view and/or manipulate clinical data (e.g., heart rate, blood pressure, etc.) using an appropriate application program. Using a manual input device in such a way is cumbersome and inadequate for a medical practitioner who needs the use of his or her hands (e.g., a surgeon who has scrubbed in and is in the process of performing a surgical operation). If the medical practitioner needed to interact with the data information system during the surgical operation, the medical practitioner would have to scrub out, ask assistants for help, and/or use specially designed touch screens within the sterile surgical environment to use the manual input device in order to control the application program. Voice control technology has been used for voice transcription in report generation and to control surgical instruments such as a surgical microscope and drill, but not for control of a data information system that displays clinical data from multiple sources.

Therefore, there is a need for a voice-controlled interface that displays clinical data that is acquired data from various devices, irrespective of the format in which the data is produced. A need further exists for the voice-controlled interface to be user-customizable so that users can operate the interface without having to become familiar with a particular set of voice commands for the interface.

SUMMARY OF THE INVENTION

Some embodiments of the invention provide a method for a voice-controlled clinical information dashboard. The voice-controlled clinical information dashboard of some embodiments includes one or more windows (or "modalities") that display clinical information (e.g., vital signs, lab results, reports, images, etc.). In some embodiments, the voice-controlled clinical information dashboard provides a set of functions (e.g., menus, buttons, etc.) that can be invoked through voice commands; these functions may manipulate the display of the dashboard and/or direct the dashboard to perform one of its operations or functions. In some embodiments, this invoking a dashboard function includes opening and closing modalities and/or dashboards, minimizing and maximizing modalities and/or dashboards, rearranging locations of modalities and/or dashboards on screen, inputting data, etc. The voice recognition functionality of some embodiments can be turned on and off as needed so that auditory commands not intended for the clinical information dashboard do not conflict with the intentions of the operator.

Some embodiments allow for a user definable and expandable set of verbal commands. In some embodiments, a user may replace a voice command (e.g., a default voice command) corresponding to a function or set of functions of the dashboard with a user-specified voice command. In some embodiments, these customizations are stored and retrieved on a "per-user" basis. In this manner, the voice commands of the voice-controlled clinical information dashboard are fully customizable and user-independent.

Some embodiments allow a voice command to be a "macro" voice command that corresponds to multiple dashboard functions (e.g., multiple buttons, menu selections, etc.). In some embodiments, a macro voice command may include one or more "top level" functions (i.e., functions that could be invoked by performing a single manual operation, such as a single mouse click), one or more "buried" functions (e.g., functions that are not displayed at the top level of the dashboard), or a combination of top level and buried functions. Examples of buried functions include image manipulation functions (e.g., increasing resolution, zooming, panning, etc.) that are invoked by invoking multiple functions (e.g., multiple mouse clicks to navigate through one or more menus).

In some embodiments, a dashboard function, or a set of dashboard functions, may be "overloaded." In other words, multiple voice commands may correspond to the same dashboard function, or set of dashboard functions. For instance, two different phrases, such as "zoom in" and "look closer," may correspond to a zoom function of the dashboard. In some embodiments, these overloaded functions are defined by a user.

In some embodiments, the set of voice commands available to a user is dynamic. In other words, different sets of voice commands may be available, depending on the data displayed in the dashboard in some embodiments. In some of these embodiments, a voice command includes the actual data displayed in the dashboard. For instance, when the dashboard displays a list of patients, a user may select a particular patient simply by saying the patient's name.

In some embodiments, an audio output device (e.g., a speaker, or set of speakers) outputs audio from the clinical dashboard. This audio may include a spoken version of text and/or other data displayed by the clinical dashboard in some embodiments.

While the above examples have illustrated the data output functionality of some embodiments of the voice-controlled clinical information dashboard, the voice command functionality may be used for data input purposes as well in some embodiments. In other words, a user may enter data using voice commands into a data object (e.g., a list) of the clinical information dashboard in addition to, or in lieu of, manually entering the data object through traditional input methods (e.g., keyboard, mouse, etc.).

In some embodiments, voice commands also control multiple application programs (e.g., the voice-controlled clinical information dashboard and one or more other application programs) running within a multi-tasking operating environment. For example, if three application programs are simultaneously operating, voice commands can be used to maximize or resize a particular application of the three application programs.

Some embodiments provide software components for performing the abovementioned functionality of some embodiments. Some of these embodiments provide a voice recognition engine, a programmatic interface between the voice recognition engine, and a set of screen-based visual controls of a voice-controlled clinical information dashboard. The voice recognition engine of some embodiments translates auditory signals into text. The programmatic interface of some embodiments converts this text into tokens. The programmatic interface of some embodiments correlates each token to a function or set of functions that can be provided to the dashboard for execution by the dashboard. In some embodiments, these functions encompass the entire functionality of the dashboard (e.g., operating a set of menus, manipulating a set of data objects appearing in or stored within either the dashboard or any associated databases serving the dashboard, etc.).

BRIEF DESCRIPTION OF THE DRAWINGS

The novel features of the invention are set forth in the appended claims. However, for purpose of explanation, several embodiments of the invention are set forth in the following figures.

DETAILED DESCRIPTION OF THE INVENTION

Figure 1:
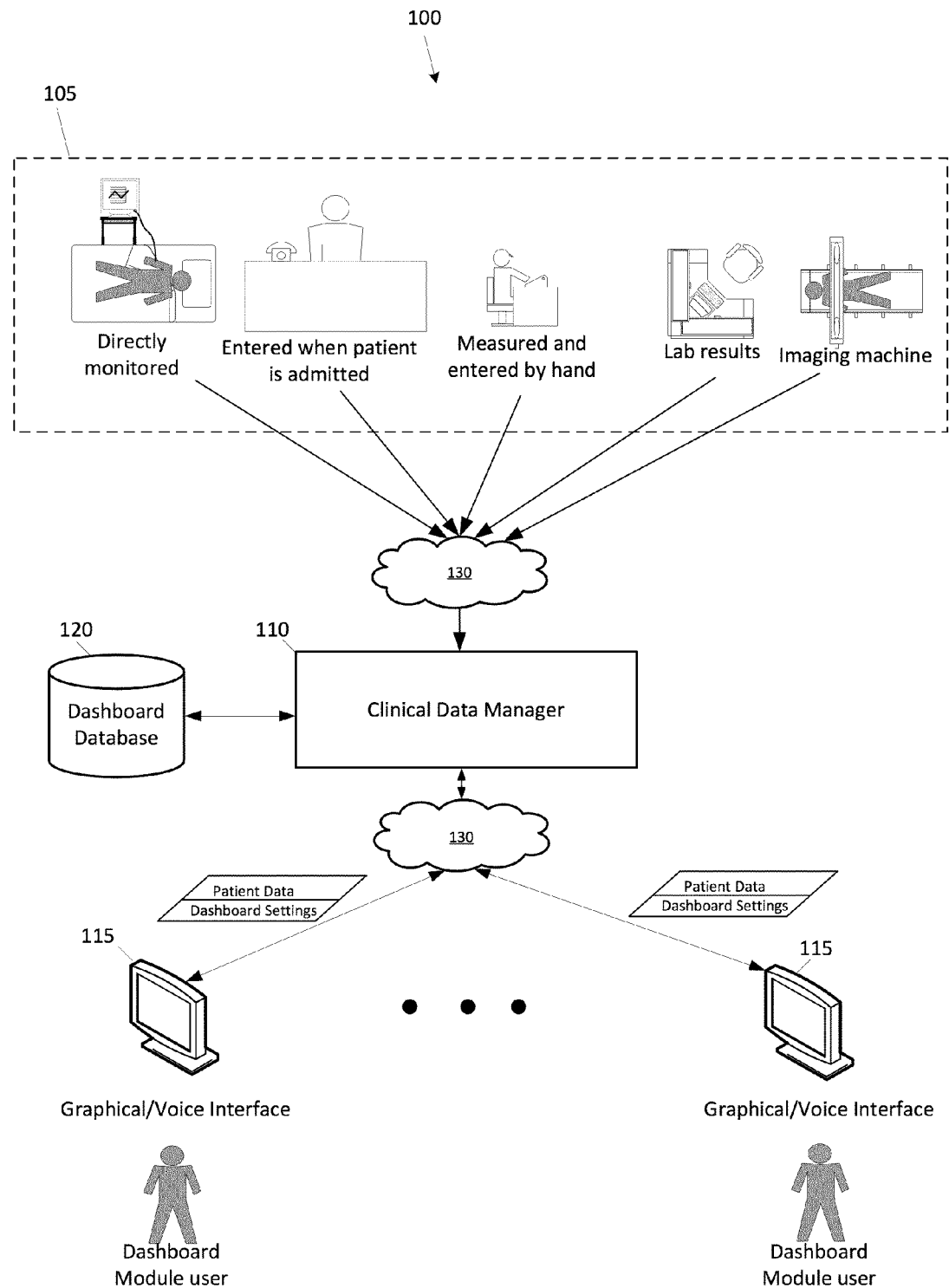
FIG. 1 illustrates a conceptual system architecture of some embodiments.

In the following description, numerous details are set forth for purpose of explanation. However, one of ordinary skill in the art will realize that the invention may be practiced without the use of these specific details. For instance, the techniques described below are described in a specified order, but other embodiments may change the order of the operations while still embodying the current invention.

I. Overview

Some embodiments of the invention provide a method for a voice-controlled clinical information dashboard. The voice-controlled clinical information dashboard of some embodiments includes one or more windows (or "modalities") that display clinical information (e.g., vital signs, lab results, reports, images, etc.). In some embodiments, the voice-controlled clinical information dashboard provides a set of functions (e.g., menus, buttons, etc.) that can be invoked through voice commands; these functions may manipulate the display of the dashboard and/or direct the dashboard to perform one of its operations or functions. In some embodiments, this invoking a dashboard function includes opening and closing modalities and/or dashboards, minimizing and maximizing modalities and/or dashboards, rearranging locations of modalities and/or dashboards on screen, inputting data, etc. The voice recognition functionality of some embodiments can be turned on and off as needed so that auditory commands not intended for the clinical information dashboard do not conflict with the intentions of the operator.

Some embodiments allow for a user definable and expandable set of verbal commands. In some embodiments, a user may replace a voice command (e.g., a default voice command) corresponding to a function or set of functions of the dashboard with a user-specified voice command. In some embodiments, these customizations are stored and retrieved on a "per-user" basis. In this manner, the voice commands of the voice-controlled clinical information dashboard are fully customizable and user-independent.

Some embodiments allow a voice command to be a "macro" voice command that corresponds to multiple dashboard functions (e.g., multiple buttons, menu selections, etc.). In some embodiments, a macro voice command may include one or more "top level" functions (i.e., functions that could be invoked by performing a single manual operation, such as a single mouse click), one or more "buried" functions (e.g., functions that are not displayed at the top level of the dashboard), or a combination of top level and buried functions. Examples of buried functions include image manipulation functions (e.g., increasing resolution, zooming, panning, etc.) that are invoked by invoking multiple functions (e.g., multiple mouse clicks to navigate through one or more menus).

In some embodiments, a dashboard function, or a set of dashboard functions, may be "overloaded." In other words, multiple voice commands may correspond to the same dashboard function, or set of dashboard functions. For instance, two different phrases, such as "zoom in" and "look closer," may correspond to a zoom function of the dashboard. In some embodiments, these overloaded functions are defined by a user.

In some embodiments, the set of voice commands available to a user is dynamic. In other words, different sets of voice commands may be available, depending on the data displayed in the dashboard in some embodiments. In some of these embodiments, a voice command includes the actual data displayed in the dashboard. For instance, when the dashboard displays a list of patients, a user may select a particular patient simply by saying the patient's name.

In some embodiments, an audio output device (e.g., a speaker, or set of speakers) outputs audio from the clinical dashboard. This audio may include a spoken version of text and/or other data displayed by the clinical dashboard in some embodiments.

While the above examples have illustrated the data output functionality of some embodiments of the voice-controlled clinical information dashboard, the voice command functionality may be used for data input purposes as well in some embodiments. In other words, a user may enter data using voice commands into a data object (e.g., a list) of the clinical information dashboard in addition to, or in lieu of, manually entering the data object through traditional input methods (e.g., keyboard, mouse, etc.).

In some embodiments, voice commands also control multiple application programs (e.g., the voice-controlled clinical information dashboard and one or more other application programs) running within a multi-tasking operating environment. For example, if three application programs are simultaneously operating, voice commands can be used to maximize or resize a particular application of the three application programs.

Some embodiments provide software components for performing the abovementioned functionality of some embodiments. Some of these embodiments provide a voice recognition engine, a programmatic interface between the voice recognition engine, and a set of screen-based visual controls of a voice-controlled clinical information dashboard. The voice recognition engine of some embodiments translates auditory signals into text. The programmatic interface of some embodiments converts this text into tokens. The programmatic interface of some embodiments correlates each token to a function or set of functions that can be provided to the dashboard for execution by the dashboard. In some embodiments, these functions encompass the entire functionality of the dashboard (e.g., operating a set of menus, manipulating a set of data objects appearing in or stored within either the dashboard or any associated databases serving the dashboard, etc.).

Section II below introduces terms and concepts relating to clinical information "dashboards." Section III provides more detail regarding the voice control functionality of dashboards of some embodiments, and various aspects of this voice control functionality. Section IV then describes a computer system in which the systems and methods of some embodiments may be implemented.

II. Overview of Clinical Information Dashboards

In some embodiments, a "dashboard" is a collection of window panes that can be part of a single visual display presentation. A clinical information dashboard of some embodiments is a dashboard where one or more of the window panes displays clinical information (such as vital statistics, lab results, or other clinical information) pertaining to one or more patients. The window panes of a dashboard can be typically collectively viewed in a display, although in some embodiments, the dashboard (and hence some of its window panes) can extend beyond the boundaries of the display.

The information displayed in a window pane (also referred to as the "view" of a window pane) may be presented in different forms, including reports, lists, notes, graphs, two-dimensional and three-dimensional images, etc. Each window pane can present one or more views of (1) one or more clinical data items (e.g., a list or graph associated with a vital signal or lab measurement) or (2) established treatment guidelines or protocols (e.g., guidelines from public reference sources or from customized intramural institutional policies regarding particular conditions or measurements). Dashboards are further described in more detail below with reference to FIG. 2, after a discussion of a clinical information system of some embodiments in which such dashboards may be incorporated.

FIG. 1 conceptually illustrates a system architecture 100 of a clinical information system which uses dashboards to interactively provide information to medical practitioners. The system architecture 100 includes several clinical data sources 105, a clinical data manager 110, a set of graphical/voice interfaces 115, a dashboard database 120, and a network 130. As shown in FIG. 1, the clinical data manager 110 receives patient data from several disparate patient data sources 105. In some embodiments, the clinical data manager 110 receives data from one or more of these patient data sources 105 through the network 130. The network 130 of some embodiments is a local area network, ("LAN"), a wide area network ("WAN"), a network of networks (e.g., the Internet), or some other network.

Examples of such sources 105 of patient data include direct monitoring (i.e., data collected from machines that are directly connected to a patient), data entered when a patient is admitted, data entered by hand (e.g., by a healthcare provider pursuant to an examination), lab results, and/or imaging machine data. Although only a few examples are mentioned, one of ordinary skill in the art would recognize that other sources of information (not shown) may provide information to the clinical data manager 110.

The clinical data manager 110 collects objective data, such as vitals from monitors monitoring the patients, lab reports, and medical images (e.g., x-rays, Magnetic Resonance Imaging ("MRI"), Computed Tomography ("CT") scans, etc.) as well as subjective data such as physicians' assessments, physicians' diagnoses, or physician treatment plans from the various data sources 105. In some embodiments, the clinical data manager 110 receives information from a dashboard database 120, which may include previously recorded patient data from any source, including any of the abovementioned sources 105. The data collected by the clinical data manager 110 may arrive from one or more locations, such as different labs, different locations within a single hospital, and/or multiple different hospitals. In some embodiments, the relevant data is not only pulled from medical facilities, but also from different servers across the Internet (e.g., library, educational institutions, etc.). Such collection of data from multiple locations is described in more detail in U.S. patent application Ser. No. 12/036,285, entitled "Patient Monitoring," filed Feb. 24, 2008, the contents of which are herein incorporated by reference.

The clinical data manager 110 of some embodiments receives, normalizes, analyzes, and/or aggregates the patient data for the purposes of gathering data about individual patients (as a snapshot of a patient's data or as a record of the data over time), and/or for the purpose of comparing statistics among patients (in some cases including the change, or "delta," in statistics of each patient) for various reasons. For instance, these statistics may be normalized and compared in order to efficiently allocate medical resources.

The clinical data manager 110 of some embodiments reports data, disseminates data, and/or alerts users to data through various clinical information interfaces 115. In some embodiments, this reporting, dissemination, and or alerting is done by transmitting patient data to the interfaces 115 through a network 130 (e.g., the Internet, a LAN, or some other network).

In some embodiments, these interfaces 115 include one or more display devices. The display devices of some embodiments include a single display device, such as a computer monitor, television screen, PDA screen, computer tablet, etc. In some embodiments, an interface 115 includes multiple display devices. In some of these embodiments, an interface 115 includes an array of display interfaces (e.g., a "data wall").

In some embodiments, an interface 115 displays one or more "intelligent" dashboards that display different data, depending on the situation. Such intelligent dashboards are further described in more detail in U.S. patent application Ser. No. 12/036,287, entitled "Intelligent Dashboards," filed Feb. 24, 2008, the contents of which are herein incorporated by reference. While the abovementioned Application describes intelligent dashboards in detail, a brief description of intelligent dashboards is provided below.

In some embodiments, the interfaces 115 of FIG. 1 display intelligent dashboards with different information from each other depending on different criteria, including the job of the user within the medical system, the particular terminal on which the interfaces 115 are displayed, and/or the momentary needs of the individual user (i.e., healthcare provider) and/or patient. In some embodiments, the intelligent dashboards of the various interfaces 115 display different information depending on where the interface 115 is located. For example, an interface 115 for a user in a cardiac intensive care unit ("ICU") may provide a dashboard with one set of data, while another interface 115 for a user in neurosurgery may provide a dashboard with a different set of data. Moreover, in some embodiments, the interface 115 may provide different information depending on a particular patient's diagnosis or condition. The clinical data manager 110 of some embodiments can also provide the data in real-time to the various interfaces 115.

In some embodiments, the dashboard database 120 stores information relating to the customization of presentation of information through the interfaces 115 based on several factors, including, as mentioned above, (1) the identity of a user of the interface 115 and/or (2) the location of a user of the interface 115. In other words, the dashboard database 120 may store settings for displaying user- and/or location-based customized dashboards. In some embodiments, these settings include a user-customized layout of modalities. The user-customized layout of some embodiments specifies location and/or size of modalities within the dashboard. These customized layouts may be modified, saved, and recalled at a later time in some embodiments.

In some embodiments, the clinical data manager 110 provides these stored settings to an interface 115 upon a request to the clinical data manager 110 by the interface 115 (e.g., when a user logs in to the interface 115). Additionally, a user may make changes to existing settings, or create new settings, at an interface 115. The dashboard database 120 may then store these settings for retrieval at a later time (e.g., when the user logs in to an interface 115 at a subsequent time).

Although FIG. 1 illustrates the interfaces 115 as sending and receiving dashboard settings from the clinical data manager 110, in some embodiments, one or more of the interfaces 115 sends and receives dashboard settings directly to and from the dashboard database 120. In some embodiments, the dashboard database 120 and the clinical data manager 110 physically reside on the same hardware (e.g., a single computer). In other embodiments, the dashboard database 120 and the clinical data manager 110 reside on separate hardware (e.g., two or more different computers). The dashboard database 120 and the clinical data manager 110 of some embodiments are communicatively coupled through a network (not shown), such as a LAN, a network of networks (e.g., the Internet), or some other network.

Some embodiments provide several manual tools for that allow user interaction with the interfaces 115 in order to access desired information. These manual tools may include traditional input devices, such as mice, keyboards, touch screens, trackpads, etc. In some embodiments, one or more of the interfaces 115 includes a voice-control input component that allows a user of the interface 115 to interact with the dashboard through voice commands. Thus, one or more of the interfaces 115 of some embodiments provide (1) a visual component (i.e., a graphical user interface, or "GUI") that interactively displays patient information and (2) an input component, which includes voice command functionality of some embodiments for interacting with the GUI. Before discussing this voice command functionality in Section III, an exemplary GUI that may be displayed on an interface 115 is discussed below with reference to FIG. 2.

Figure 2:
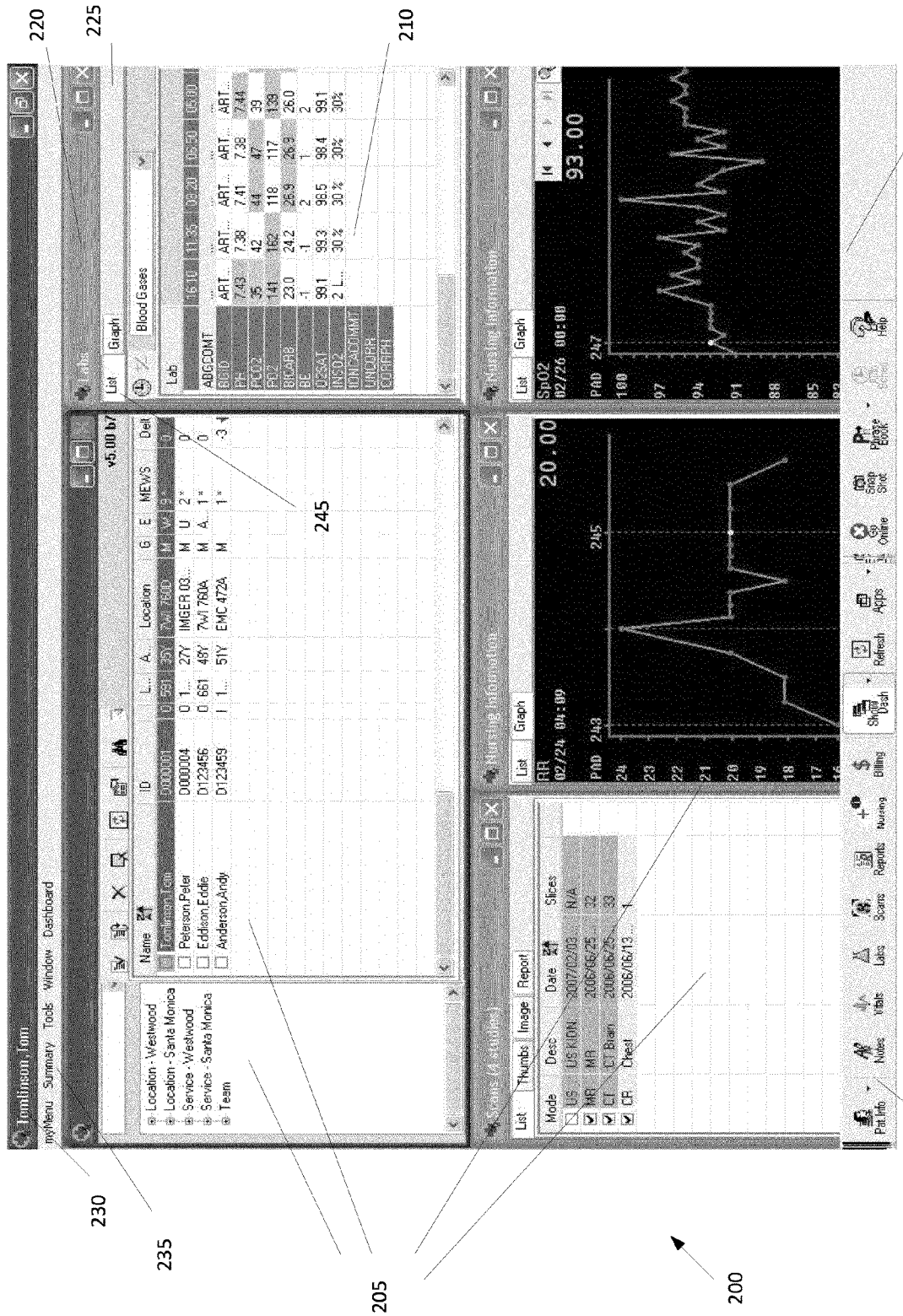
FIG. 2 illustrates an example of a dashboard of some embodiments.

FIG. 2 illustrates an example of a GUI 200 that may be displayed by an interface 115 of FIG. 1. As shown in FIG. 2, the GUI 200 includes a title bar 230 and a display area for displaying one or more window panes (or "modalities") 205, 210, and 215. Some embodiments provide a set of user interface tools for invoking various functions of the GUI 200 (e.g., functions to manipulate the display of the GUI 200, or any other function of the GUI 200), including a menu bar 235 and a master toolbar 240. The master toolbar 240 appears at the bottom of the GUI 200 and contains easy access to different application functionalities. For example, the master toolbar 240 might include a button to refresh the clinical data, view lab results, view billing information, open other windows, etc.

Several of the windows in the GUI 200 display clinical data for one or more patients. The information displayed in a window pane 205 includes patient data in any form (e.g., reports, lists, notes, graphs, images, etc). For example, the information displayed may include the data needed to assess the severity of the patient's condition, the trend (e.g., improving and deteriorating) of the condition, the cause of the condition, the secondary consequences of the condition, etc. As illustrated, each window pane 205 can optionally have a title bar 220 that displays information about the window and a menu bar 225 that may include user interface tools, such as selectable tabs, a pull-down menu, a search bar, or any other user interface tool.

Several of the window panes 205 present different views of one or more clinical data items. For instance, a particular window pane 210 provides a view for displaying a lab report for "blood gases" of a patient. The lab report is presented as a list of measurements for several blood gases. In some cases, a particular item on the list can be expanded to present additional detail. However, the lab report can also be presented as a graph by selecting the item in the list and selecting a tab 245 in the menu bar 225. The lab report can be presented as a graph by simply selecting the item in the list (e.g., by double clicking the item with a cursor control device, such as a mouse, or through a voice command, as further discussed below).

The view provided by another window pane 215 is an example of such a graph that depicts one of the blood gases described in the window pane 210. Specifically, the graph of window pane 215 indicates the percentage of oxygen saturation in blood ($SpO_2$) of the patient over a period of time. As mentioned above, the information that is displayed in the dashboard may also include established treatment guidelines, or protocols (not shown). Such guidelines may come from public reference sources, or from customized intramural institutional policies. For instance, when a patient is diagnosed with hyperglycemia, one of the views of a dashboard may present a hospital's policy on how the condition is treated.

In some embodiments, the collection of one of more window panes 205, 210, and 215 is referred to as a single dashboard. Two or more such dashboards can be "linked" together such that, while viewing a first dashboard, a second dashboard can be opened (i.e., displayed) upon selection of an item in the first dashboard. When the second dashboard is opened, the first dashboard may be automatically minimized, hidden or, in some embodiments, closed. Also, in some embodiments, when the second dashboard is opened, the first dashboard can be arranged in a manner so that both dashboards can be viewed concurrently.

The linking of the dashboards can be based on what the user most wants to see. Specifically, the information that is displayed in one or more views of the dashboard is designed and configured with the intent of following the typical train of thought and sequence of assessments of a trained or experienced professional, such as a doctor. For example, one dashboard might link to a spreadsheet of the ten most relevant lab results over time, while another dashboard might lead to a trend plot of one or two key lab results over time. This allows a user of the dashboard (e.g., a healthcare provider, such as a physician) to obtain the most relevant information without having to unnecessarily sort through unmanageable masses of information.

For instance, the selected item in the parent dashboard may be a vital sign, such as current blood pressure. Selecting the blood pressure in the parent dashboard may open a new "drilldown" dashboard, which displays information related to the selected item (i.e., blood pressure). The drilldown dashboard may display more detailed information about the blood pressure, such as trends, calculations, components of the selected statistic, etc. The drilldown dashboard may also display related information (e.g., heart rate, respiratory rate, etc.). More detailed information about drilldown dashboards can be found in U.S. patent application Ser. No. 12/036,281, entitled "Drill Down Clinical Information Dashboard," filed Feb. 24, 2008, the contents of which are herein incorporated by reference.

In addition to the linking of dashboards, a dashboard can be opened up to a predefined configuration. In this way, the user is initially presented with the most relevant information. For example, rather than starting with a view containing a list of all radiology scans of a patient, the dashboard may be configured to start with a view of a current chest x-ray and a view of a previous chest x-ray. Therefore, instead of pulling data out by a pull model (e.g., selecting different links to receive the relevant data), the dashboard can utilize a push model that pushes the relevant data out as a first view. The different configurations of the dashboards can be provided and stored in the dashboard library or database 120 as shown in FIG. 1.

While some specific examples of GUI controls (e.g., menu bar 225) were specifically shown in FIG. 2, one of ordinary skill in the art would recognize that other GUI controls that are not shown may be included in a dashboard. For instance, a button, a menu, a menu item, a list, a list box, a list item, a combo box, a radio button, a check box, a text area, a text pane, a scroll bar, a cursor, and/or a slider could be used for various purposes within a dashboard.

III. Voice-Controlled Dashboard

As discussed above, the dashboards displayed by the interfaces 115 of the clinical information system described above are interactive. In other words, a user may manipulate the dashboards in myriad ways (e.g., drill down, open related dashboards, change the orientation of modalities within a dashboard, etc.) in order to access useful information. A user may also use the dashboards for other functions as well (e.g., inputting data, such as clinical data). These functions may perform control operations on user interface controls of the dashboard, such as selecting menu items in a menu bar, selecting tabs, double-clicking, right-clicking, etc. As mentioned above, some embodiments provide traditional input mechanisms, such as mice, keyboards, touch screens, scroll wheels, trackpads, etc. for manually performing one or more of these operations by hand. In addition to, or in lieu of, these traditional input mechanisms, some embodiments provide a voice-controlled clinical information dashboard, which includes voice control functionality for performing one or more functions of a dashboard through voice commands. More details regarding this voice control functionality are provided below in Sections B-J, after a discussion of the software architecture of some embodiments.

A. Software Architecture

Figure 3:
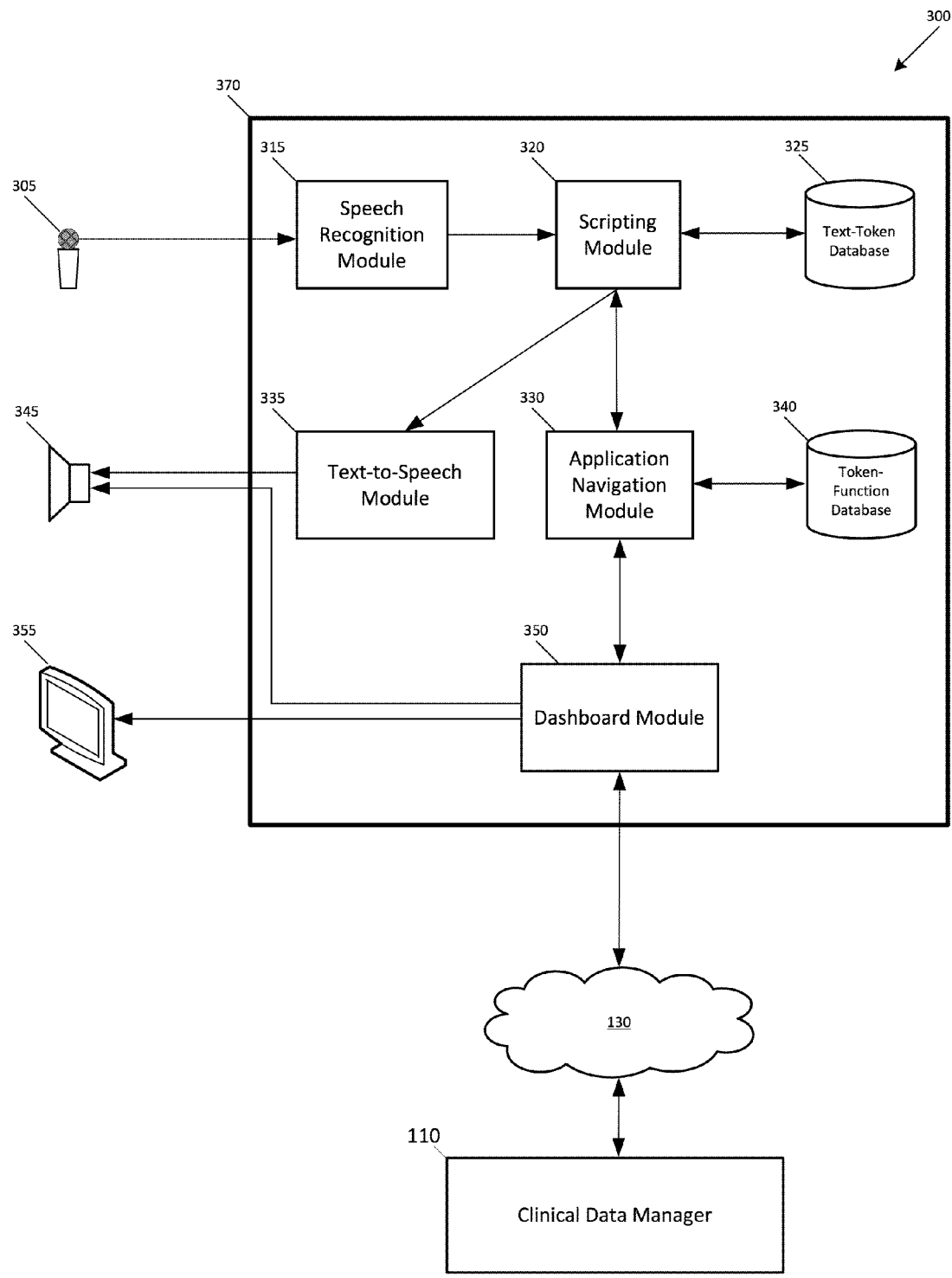
FIG. 3 illustrates a software architecture of some embodiments.

In some embodiments, voice control functionality of a voice-controlled clinical information dashboard is implemented at least partially by software that runs on a hardware interface adjacent to a speaker (e.g., a healthcare provider). FIG. 3 conceptually illustrates an interface 300 of some embodiments which displays a dashboard that may be controlled by voice commands. The interface 300 of some embodiments is an example of an interface 115 shown in FIG. 1. The interface 300 includes a computing device 370 (e.g., a desktop computer, laptop, PDA, etc.) attached to a speech input device 305 (e.g., a microphone), a video display 355 (e.g., computer monitor, PDA screen, etc.), and an optional auditory output device 345 (e.g., a set of speakers). The interface 300 of some embodiments also includes other input devices not shown in FIG. 3 (e.g., mouse, keyboard, touchscreen, trackpad, etc.).

The computing device 370 of some embodiments runs several software modules. As shown in FIG. 3, these software modules include a speech recognition module 315, a scripting module 320, an application navigation module 330, a dashboard module 350, and an optional text-to-speech module 335. The computing device 370 of some embodiments also includes two databases: a text-token database 325 and a token-function database 340.

In some embodiments, one or both of the databases 325 and 340 are implemented through a database application (e.g., standard query language, or "SQL"). One or both of these databases 325 and 340 may be implemented as files residing in one or more memories (e.g., hard drive, random access memory ("RAM"), etc.) of the computing device 370 in some embodiments. These files include machine-readable code (i.e., compiled code) in some embodiments, while in other embodiments, these files include human-readable code (i.e., code that can be read and modified by a human). One or both of these databases 325 and 340 of some embodiments physically reside on a location external to the computing device 370 (e.g., on a server that the computing device accesses through a network 130, such as a LAN or the Internet).

In some embodiments, the dashboard module 350 is a software module that displays, through the output device 355 (e.g., one or more computer monitors in some embodiments), a dashboard. An example of such a dashboard displayed by the dashboard module 350 is described above with reference to the GUI 200, shown in FIG. 2. As mentioned above, data displayed by the dashboard module 350 is provided through a network 130 (e.g., a LAN, the Internet, or some other type of network) by a clinical data manager 110 in some embodiments. The dashboard module 350 of FIG. 3 also includes a programmatic interface to the application navigation module 330. As further described below, through this programmatic interface, the dashboard module 350 receives instructions to perform functions, as well as to output data (e.g., the content displayed by the dashboard module 350) to the application navigation module 330. The dashboard module 350 also includes an interface (i.e., a driver interface in some embodiments) to an audio output device 345 (e.g., an audio speaker or set of audio speakers).

In some embodiments, the speech recognition module 315 receives user speech from the speech input device 305, converts the received speech into text, and provides the text to the scripting module 320. The scripting module 320 of some embodiments has four modes: (1) "command" mode, (2) "text input" mode, (3) "text-to-speech" mode, and (4) "off" mode. In some embodiments, "command" mode, which is further described below, is the default mode of operation of the scripting module 320. In "off" mode, the scripting module 320 of some embodiments performs no functions and passes no data to other modules, thus avoiding unintentional voice commands being issued. The scripting module 320 of some embodiments can be set to "off" mode by providing a voice command (e.g., "stop listening") that the scripting module 320 accepts as a command. In some embodiments, the scripting module 320 can be set to "command" mode from "off" mode by providing a voice command (e.g., "start listening") that the scripting module 320 accepts as a command. Some embodiments provide other types of control in lieu of, or in addition to, voice commands (e.g., mouse, keyboard, foot pedal, etc.) in order to change the mode of the scripting module 320.

The other three modes of the scripting module 320 (i.e., "command," "text-to-speech," and "text input") further dictate how the scripting module 320 interacts with the other software modules, and will be further described below. Together, the text-token database 325, the application navigation module 330, and the token-function database 340 serve as a programmatic interface between the speech recognition module 315 and the dashboard module 350 in order to provide voice control functionality to the dashboard module 350. The functionality of these modules 320 and 330 and databases 325 and 340 is described below with reference to FIGS. 4-20.

Figure 4:
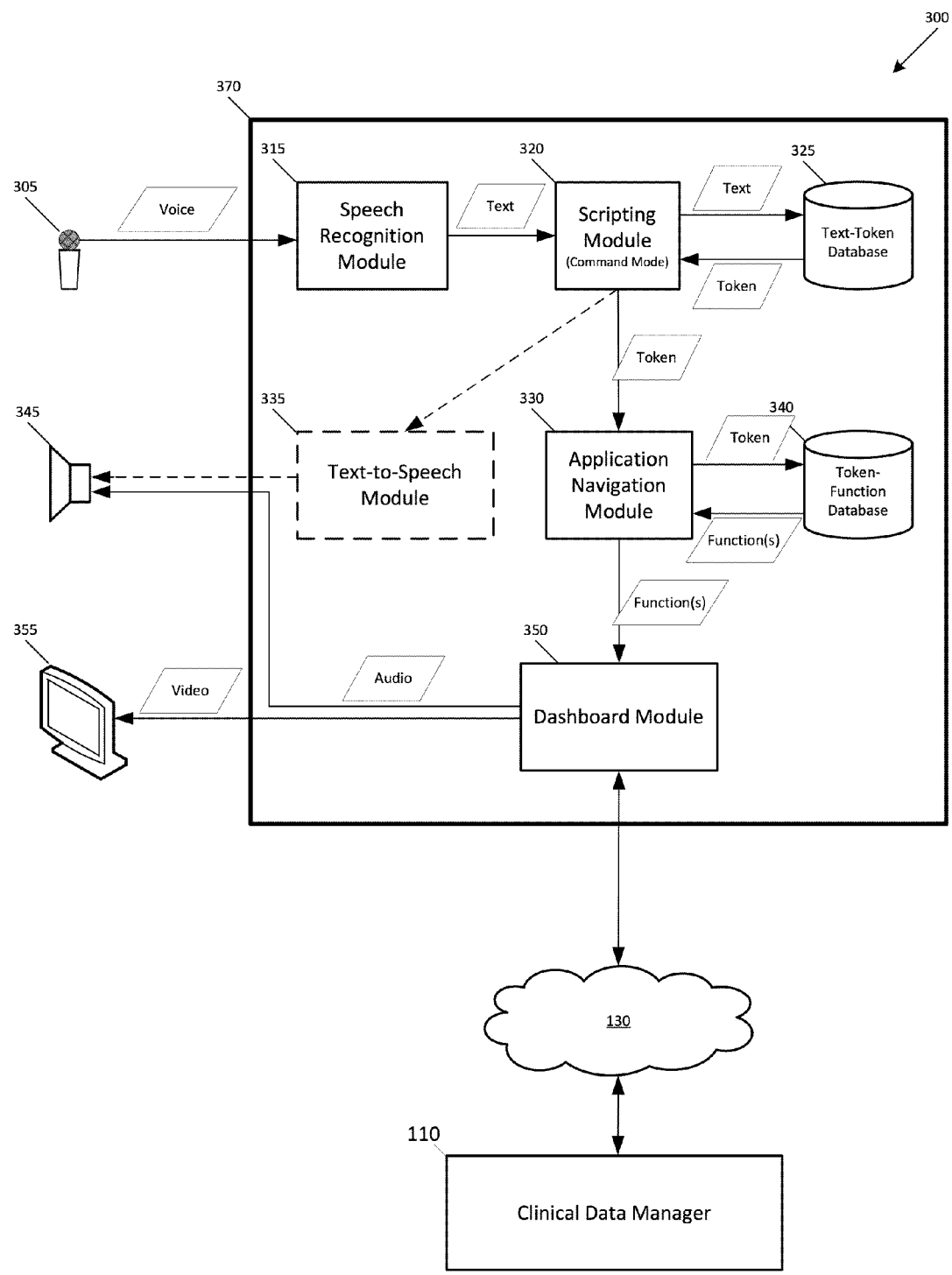
FIG. 4 illustrates data flow in "command" mode of some embodiments.
Figure 6:
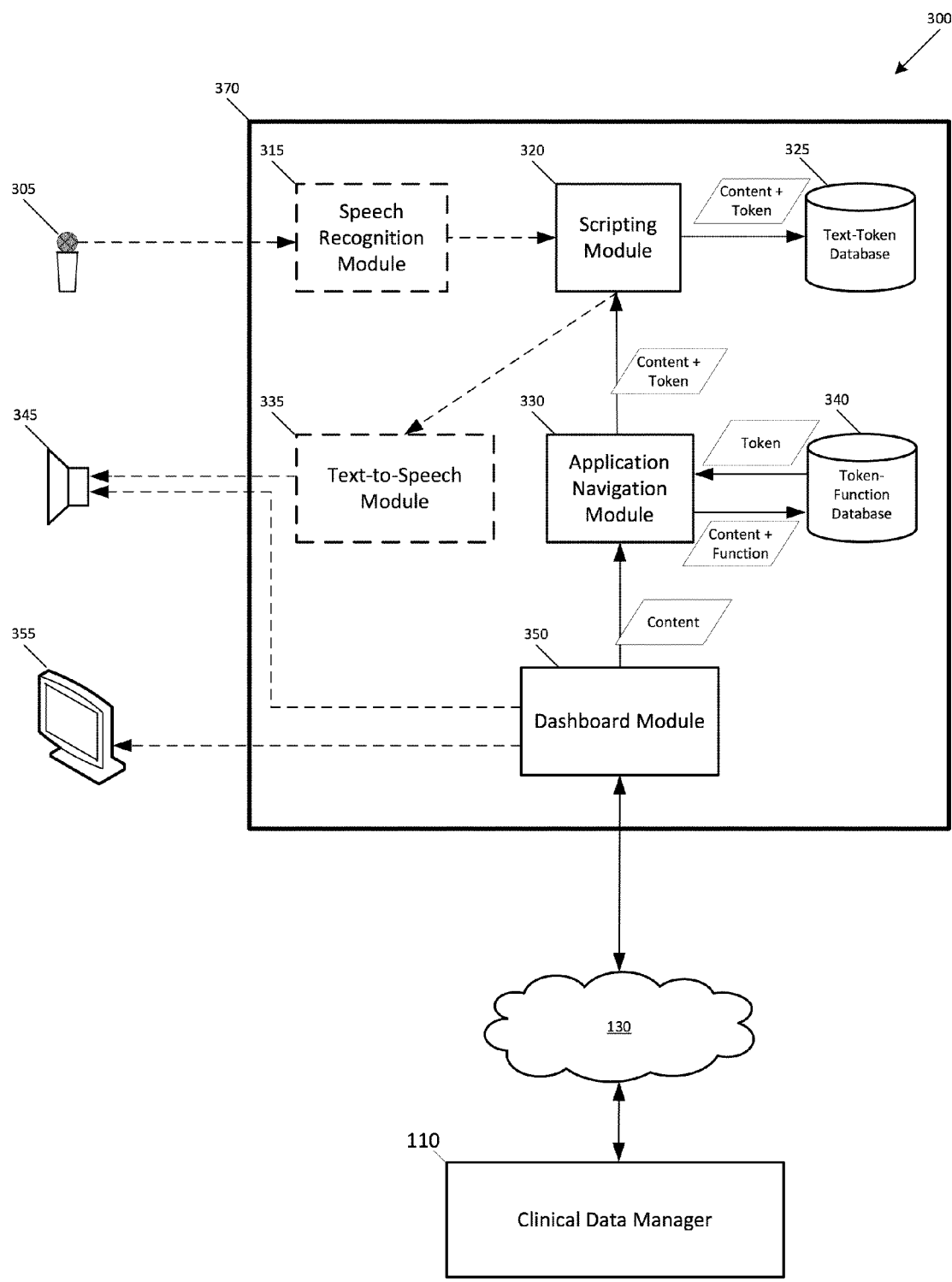
FIG. 6 illustrates data flow for dynamic voice commands of some embodiments.
Figure 19:
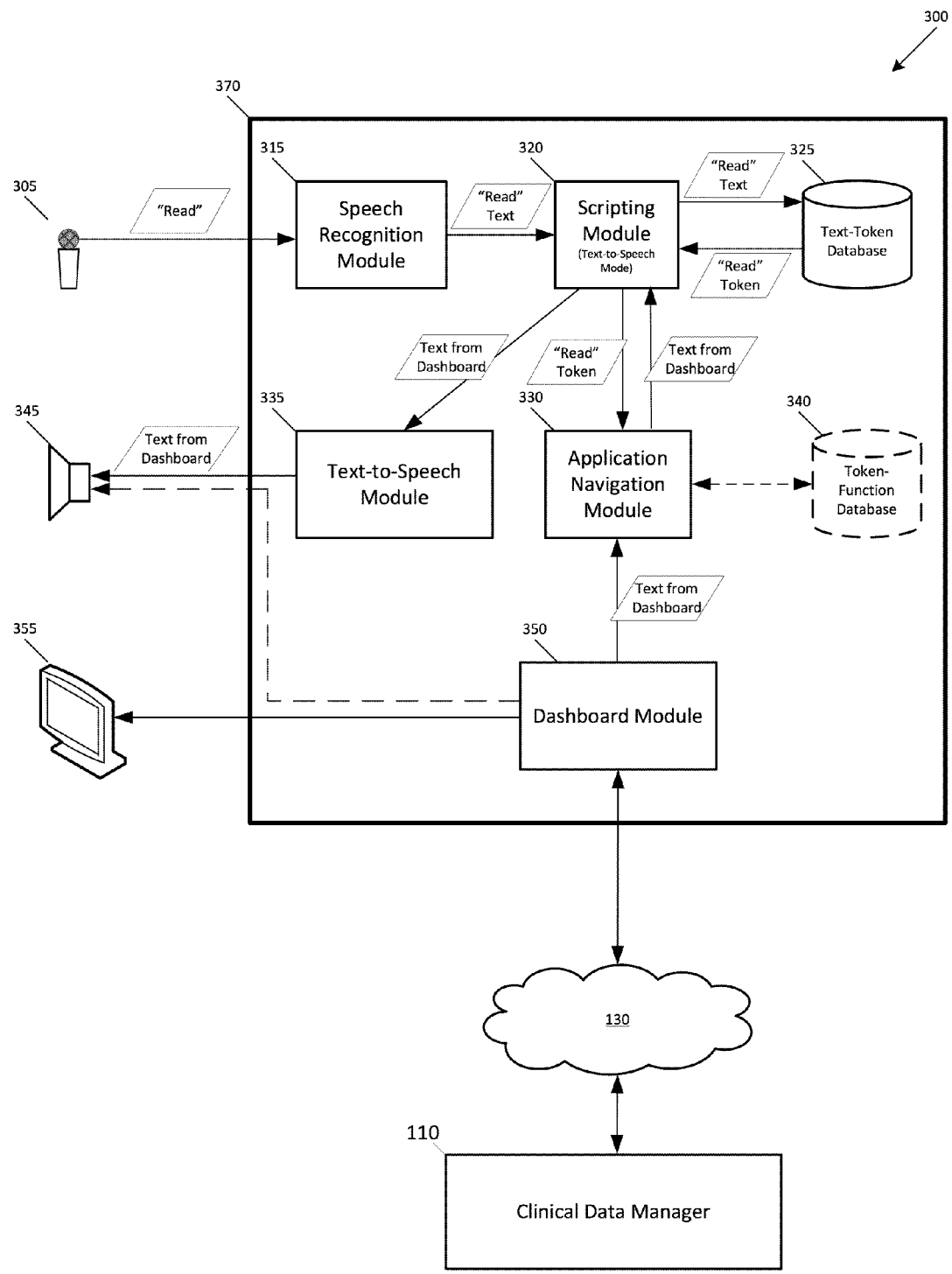
FIG. 19 illustrates data flow in text-to-speech mode of some embodiments.

As mentioned above, FIG. 3 conceptually illustrates the various software modules and databases that perform the voice control functionality of some embodiments. As such, the data flow illustrated by FIG. 3 and similar subsequent figures are conceptual. In some embodiments, two or more of the modules and/or databases described may be combined to perform the same or similar functionality as described for these modules. Combining software modules and/or databases may conceptually change the data flow described for these components. However, one of ordinary skill in the art would realize that the different data flow of some embodiments would achieve the same results of the invention without departing from the scope of the invention. FIGS. 4, 6, and 19, described below, illustrate some examples of various different data flows between the software modules and databases of FIG. 3 that allow for various different functionalities of some embodiments.

B. Command Mode

As mentioned above, in some embodiments, the voice control functionality of dashboards includes the ability to control a dashboard through voice commands. FIG. 4 illustrates the data flow of the software modules of the interface 300 shown in FIG. 3 when a voice command is initiated in order to control a dashboard.

In some embodiments, a user (e.g., a healthcare provider, such as a surgeon) issues a voice command, which the speech recognition module 315 receives through the speech input device 305. The speech recognition module 315 converts the received speech into recognized text. The speech recognition module 315 of some embodiments may be a standard "off-the-shelf" software module (e.g., VR Commander by Interactive Voice Technologies, Inc, or some other software module with the capability to convert speech into recognized text). In some embodiments, the speech recognition module 315 includes a software interface that writes the converted text to a file that is stored in a memory (e.g., hard drive, RAM, etc.) of the computing device 370. The speech recognition module 315 of some embodiments includes a software interface that allows the speech recognition module 315 to pass the converted text to other software modules.

Through one of these software interfaces, the speech recognition module 315 passes the recognized text to the scripting module 320. The scripting module 320 includes an interface for receiving the recognized text from the speech recognition module 315, as well as an interface to the text-token database 325. As mentioned above, the text-token database 325 resides on the same computing device 370 in some embodiments. In other embodiments, the text-token database 325 does not reside on the same computing device 370, but rather resides at an external location (e.g., a server).

As shown in FIG. 4, the scripting module 320 is in "command" mode. In this mode, when the scripting module 320 receives recognized text from the speech recognition module 315, the scripting module 320 treats the recognized text as a potential voice command to translate and ultimately provide to the dashboard module 350.

In some embodiments, in "command" mode, the scripting module 320 determines whether the text-token database 325 contains a token that matches the recognized text. The scripting module 320 of some embodiments makes this determination automatically (i.e., without human intervention) by formulating a database query. In some embodiments, the scripting module 320 forms this query using a previously defined script. For instance, the scripting module 320 may receive the recognized text, "zoom in." The scripting module 320 may use the previously defined script to automatically form a query, using the received recognized text as a parameter of the query.

For instance, if the text-token database 325 is implemented as an SQL database, the scripting module 320 may form an SQL query. An exemplary SQL query formed by the scripting module 320 to find a corresponding token in this example is as follows:

SELECT Token FROM TextTokenDB WHERE Text='zoom_in';

where TextTokenDB is the name of an SQL table that represents the text-token database 325, Token is the name of a column that stores tokens, and Text is the name of a column that stores converted text values that correspond to tokens.

This query would return a value (i.e., a token) if the converted text (i.e., "zoom in") has a corresponding token in the text-token database 325. For instance, a row in the table may have a row with zoom_in in the Text column and ZoomIn( ) in the Token column. On the other hand, if the converted does not correspond to a token in the text-token database 325, then the query would return a null value, thus indicating that there is no corresponding token for the converted text in the text-token database 325.

Upon determining that a matching token does not exist in the text-token database 325 (i.e., the query returns a null value), the scripting module 320 of some embodiments holds the recognized text for some amount of time in memory in case subsequent recognized text, in conjunction with the present recognized text, is associated with a token in the text-token database. This amount of time is a predetermined time limit (e.g., five seconds, ten seconds, etc.) in some embodiments, while in other embodiments, this amount of time is an indefinite amount of time. In lieu of storing recognized text when a corresponding token is not found, the scripting module 320 of some embodiments simply discards the recognized text (i.e., performs no function based on the recognized text and does not store the recognized text in memory).

On the other hand, upon determining that there is a matching token in the text-token database 325, the scripting module 320 of some embodiments provides the matching token to the application navigation module 330, which includes an interface to the token-function database 340. As with the text-token database 325, the token-function database 340 resides on the computing device 370 in some embodiments, while in other embodiments, the token-function database 340 resides externally to the computing device 370. The application navigation module 330 determines whether the token-function database 340 includes a function (or set of functions) that matches the provided token. In some embodiments, this determination made by the application navigation module 330 is similar to the determination made by the scripting module 320 (e.g., a database query in a query language, such as SQL).

While the determinations described above (i.e., the queries performed by the scripting module 320 and/or the application navigation module 330) involve performing database queries, some embodiments check the presence of corresponding tokens or functions in a different manner. For instance, some embodiments use other data storage and searching methodologies (e.g., XML, plain text, object-oriented databases, etc.). In some embodiments, one or both of the databases are implemented as plain text files with comma separated values. These plain text files can be searched systematically in order to determine whether corresponding values are present. An example of such plain text file could be organized with comma separated values text, token on each line. Such a file could be traversed line by line in order to determine whether a corresponding token is present for a given converted text value. One skilled in the art would recognize that such files could be traversed using standard programming libraries (e.g., fstream, iostream, java.io, etc.).

Upon determining that the token-function database 340 does not contain a matching function, the application navigation module 330 of some embodiments discards the received token (i.e., the application navigation module 330 performs no further operation based on the received token). However, upon determining that the token-function database 340 does include a matching function (or set of functions), the application navigation module 330 provides the matching function (or set of functions) to the dashboard module 350 for execution. In some embodiments, the providing of the function (or set of functions) is done through a programmatic interface between the application navigation module 330 and the dashboard module 350.

In some embodiments, the dashboard module 350 has the capability to execute the function (or set of functions) received from the application navigation module 330. In other words, the function (or set of functions) includes instructions that are executable by the dashboard module 350. These instructions provided to the dashboard module 350 include compiled machine code (which is not readable by a human) in some embodiments, while in other embodiments, the instructions provided to the dashboard module 350 include code that is readable by a human. In some embodiments, a particular received function may correspond to a user interface control (e.g., a button, a menu item, etc.) of the dashboard module 350. As further discussed below, the providing of one or multiple functions from the application navigation module 330 to the dashboard module 350 provides a rich set of voice controls for interfacing with the dashboard module 350 in order to perform any function that could be performed through manual input mechanisms (e.g., mouse, keyboard, etc.).

Figure 5:
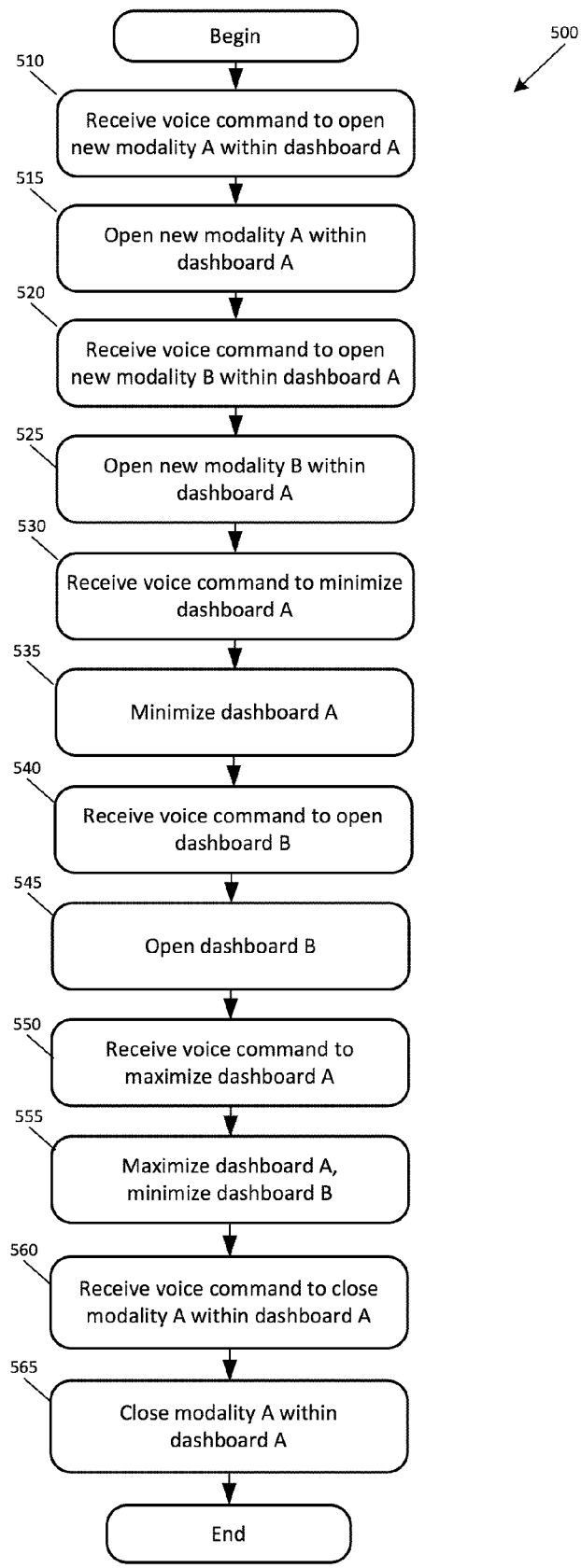
FIG. 5 illustrates an exemplary process of several dashboard functions that can be invoked through voice commands.

As mentioned above, any functionality of the dashboard module 350 may be controlled through voice commands. In some embodiments, examples of this functionality include the opening and closing of modalities within a dashboard, minimizing and maximizing modalities and/or dashboards, opening and closing multiple dashboards, moving modalities within a dashboard, moving dashboards on a screen, inputting data, etc. FIG. 5 illustrates an exemplary process 500 of executing some of these functions through voice commands. In some embodiments, the process is performed by an interface 300 as described above with reference to FIG. 3. The process receives (at 510) a voice command to open a new modality ("modality A") within a dashboard ("dashboard A"). The process opens (at 515) a new modality ("modality A") within dashboard A. In some embodiments, dashboard A is shown in of the GUI 200 illustrated in FIG. 2, while modality A is an example of the "Labs" modality 210 of FIG. 2.

The process then receives (at 520) a voice command to open another new modality ("modality B") within dashboard A. In some embodiments, modality B is an example of the graph modality 215 shown in FIG. 2. In response, the process opens (at 525) modality B within dashboard A. The process then receives (at 530) a voice command to minimize dashboard A. In response, the process minimizes (at 535) dashboard A. The process receives (at 540) a voice command to open a second dashboard ("dashboard B"). The process opens (at 545) dashboard B. The process then receives (at 550) a voice command to maximize dashboard A.

The process maximizes (at 555) dashboard A. The maximizing of dashboard A also causes the minimizing of dashboard B. In some embodiments, dashboard B is not minimized. In some of these embodiments, the two dashboards are displayed together side by side. The process then receives (at 560) a voice command to close modality A within dashboard A. The process then closes (at 565) modality A within dashboard A. The process then ends.

As mentioned above, the process 500 illustrated in FIG. 5 is merely provided as an example of the many dashboard functions that can be invoked by voice commands. In some embodiments, other dashboard functions can be performed (e.g., exit program, log in, etc.) through voice commands. Some other examples of voice commands that correspond to dashboard functions are provided in Table 1, below.

In some embodiments, a voice command corresponds to a logical dashboard function (or set of functions). For instance, the voice command "exit dashboard" may close the dashboard. On the other hand, in some embodiments, a series of voice commands corresponds to a combinatorial voice command that represents a logical flow of commands. An example of such a combinatorial command is the combination of two voice commands: "select" and "modality one." In some embodiments, neither the "select" command nor the "modality one" command alone perform a function. However, together, they form a combinatorial voice command that selects a modality of the dashboard named "modality one."

While several examples are described in which one application program (e.g., a dashboard module 350) executes functions based on voice commands, some embodiments provide voice command functionality for multiple application programs. In some of these embodiments, one or more the multiple application programs is not a clinical information dashboard. Some embodiments provide multiple application navigation modules (not shown), one for each application program that is to be controlled by voice commands. In some embodiments, the scripting module 320 includes a programmatic interface with each of these application navigation modules. In some of these embodiments, the text-token database 325 correlates recognized text not only to tokens, but also to the application program to which the recognized text corresponds.

1. Dashboard Feedback when Receiving Commands

A dashboard module (such as the dashboard module 350 discussed with reference to FIG. 4, above) of some embodiments provides feedback to a user when the dashboard module 350 receives an instructed to perform a function or set of functions. In some embodiments, the dashboard module 350 provides feedback when receiving instructions to perform a function (or functions) as invoked by a manual input mechanism (e.g., mouse, keyboard, etc.) a voice command, or both.

In some embodiments, this feedback is visual feedback. The dashboard module 350 of some embodiments displays visual feedback on an output device (e.g., display 355 shown in FIG. 4). Visual feedback may include the text recognized by the speech recognition module. In some of these embodiments, although not shown, the scripting module 320 provides the recognized text to the application navigation module 330. The application navigation module 330 of some embodiments, after retrieving the recognized text, provides a command to the dashboard module 350 to display the recognized text. In some embodiments, the application navigation module 330 provides this display command to the dashboard module 350 in addition to a function (or set of functions) that corresponds to a token that is based on the recognized text.

The application navigation module 330 of some embodiments only provides the command to display the recognized text when the recognized text is associated with a function or set of functions that are executed by the dashboard module 350 (i.e., the recognized text has an associated token, which in turn has an associated function or set of functions). In some embodiments, the application navigation module 330 provides the command to display the recognized text even when the recognized text does not correspond to any function of the dashboard module 350. This visual feedback helps a user verify whether a desired command was recognized properly by the voice command dashboard module 350.

In some embodiments, the dashboard module 350 provides other visual feedback in combination with, or in lieu of, the displaying of the recognized text. This other visual feedback may include a visual cue, such as a highlight of a relevant portion (e.g., a button, menu item, list item, entry in a table, etc.) of the dashboard to indicate what function has been performed by the dashboard module 350 in response to a voice command. In some of these embodiments, the application navigation module 330 provides a command to the dashboard module 350 to display one or more of these other types of visual cues.

Furthermore, in addition to, or in lieu of visual feedback, some embodiments provide audio feedback to voice commands. As shown by FIG. 3, the dashboard module 350 of some embodiments includes an interface to an audio output device 345, through which the dashboard module 350 can provide such audio feedback. The audio feedback may include a sound (e.g., a beep, a chime) that indicates that the dashboard module 350 has received and successfully executed a voice command. In some embodiments, a different sound indicates that the dashboard module 350 has received, but not successfully executed a voice command. Such unsuccessful execution could be a result of the recognized text not correlating to a token, or some other error.

In some embodiments that provide audio feedback in response to voice commands, the application navigation module 330 provides the dashboard module 350 with a command to provide the audio feedback (e.g., a command to play one or more audio files). As mentioned above, the application navigation module 330 of some embodiments may command the dashboard module 350 to play different audio files depending on whether the recognized text ultimately corresponds to a function (or set of functions) of the dashboard module 350.

In addition to, or in lieu of, the dashboard module 350 providing audio and/or visual feedback, the speech recognition module 315 of some embodiments provides this feedback. In some embodiments, the speech recognition module 315 includes an interface (e.g., a driver interface, not shown) to the video output device 355. Through this interface, the speech recognition module of some embodiments 315 displays all of the text that it recognizes and passes to the scripting module 320. In some embodiments, the speech recognition module 315 includes an interface (e.g., a driver interface, not shown) to the audio output device 345. Through this interface, the speech recognition module 315 provides audio feedback (e.g., a beep, a chime, etc.) when the speech recognition module 315 converts speech to text.

C. Customizable Voice Commands

The voice command functionality of some embodiments provides flexibility in voice commands that a user may use in order to interact with a dashboard. In some embodiments, a user is able to specify any voice command for any function of the dashboard. For instance, a default voice command for a zoom operation may correspond to the speech "zoom in."

However, a user may want to replace that voice command with a different, more intuitive command, such as "look closer." Because the user is able to specify his or her own commands, it is not necessary for the user to memorize a list of commands that the user did not create.

In some embodiments, this change is made by modifying an entry in the text-token database 325 shown in FIG. 3. For example, a user may desire to replace a voice command associated with a dashboard function with a different voice command. For example, before modification, the text-token database 325 may contain an entry correlating the text "zoom in" to a token, such as ZoomIn( ). In order to replace this entry, some embodiments delete this entry and add a new entry correlating the text "look closer" with the same token (i.e., ZoomIn( )). Some embodiments allow a user to add a new voice command (e.g., "look closer") that correlates to a token (e.g., ZoomIn( )) without deleting the old voice command (e.g., "zoom in") to create an "overloaded" dashboard function, as further described below.

In some embodiments, a user performs this modification of the text-token database through the scripting module 320 described above. In some of these embodiments, the scripting module 320 includes a GUI that allows a user to make this modification graphically, while the scripting module 320 performs the back-end operations that modify the text-token database 325 (e.g., the abovementioned SQL commands in some embodiments). The scripting module 320 generates a script (i.e., a program that executes without human intervention) that performs such a modification in some embodiments, while in other embodiments, a user modifies the text-token database 325 directly. In other words, if the text-token database 325 is implemented as an SQL database, the user would issue a series of SQL commands (e.g., through a command line interface) to delete an old entry and add a new entry.

D. Dynamic Voice Commands

In some embodiments, the voice commands that are available to a user are dynamic. In other words, depending on what data is displayed in a particular dashboard (e.g., which modalities are displayed), the voice commands a user may use to manipulate (e.g., modify the layout and/or content, input data, etc.) the dashboard are different. For instance, a first dashboard may include a window that displays picture of an x-ray. The set of commands for that dashboard may include image-specific commands, such as "zoom in," and "zoom out." The set of commands may also include commands specified by the user as relating to images (e.g., the user may indicate that when an image is displayed in a dashboard, the custom voice command "make it bigger" zooms in).

When the first dashboard is closed and a second dashboard without an image is displayed, a different set of commands may be available. For instance, the command "zoom in," which may be specified as only pertaining to dashboards with images, would have no effect. However, if the second dashboard includes a list (e.g., a list of vital signs, a list of patients, etc.), list-specific commands may be available. For instance, the command "sort by column 1 ascending" may cause the list to be sorted, with the first column as the sorting criteria, in ascending order. In some embodiments, such a list-specific command would have no effect in a dashboard that does not display a list (e.g., a dashboard that displays an image but no list).

In some embodiments, the set of available voice commands for a dashboard may be tailored not only to the type of information displayed in the dashboard, but to the information itself. Thus, the set of available voice commands may include voice commands that are not coded or defined beforehand by a programmer (e.g., a programmer of the scripting module 320 and/or the application navigation module 330). Rather, the available voice commands are generated when new data is received in the dashboard. For instance, if a dashboard displays a list of patients, the set of available voice commands of some embodiments allows a user to specifically identify a patient from the list. Such a command may be "select John Doe," where John Doe is a patient displayed in the list. Alternatively, in some embodiments, the command may simply be "John Doe."

In some embodiments, each time new information is displayed in a dashboard (e.g., when a dashboard is first instantiated, when data is updated in a dashboard, when a new modality is opened in a dashboard, etc.), the set of available voice commands is updated to include some or all of the content displayed in the dashboard. FIG. 6 conceptually illustrates the flow of information between the dashboard module 350, the application navigation module 330, the scripting module 320, the token-function database 340, and the text-token database 325) when the dashboard module 350 displays such new information. In this figure, software modules (e.g., speech recognition module 315) that are not discussed with reference to the data flow illustrated by FIG. 6 are drawn with a dashed line. However, in some embodiments, these modules are still present.

In some embodiments, the application navigation module 330, through its interface with the dashboard module 350, detects that new content is displayed in the dashboard module 350. The dashboard module 350 of some embodiments provides data to the application navigation module 330 indicating what content is displayed in the dashboard module 350. In some of these embodiments, the dashboard module 350 provides data about its content to the application navigation module 330 each time new content is loaded into or displayed by the dashboard module 350. The dashboard module 350 of some embodiments provides data about its content to the application navigation module 330 each time content is removed from, or no longer displayed by, the dashboard module 350.

The application navigation module 330 analyzes the content of the dashboard module 350 in order to determine whether the content can be controlled by a voice command. In some embodiments, this determination is based on predefined parameters, such as data type. For instance, an example data type that could be identified as controllable through voice commands is patient names.

Thus, when new patients are displayed in the dashboard (e.g., when a patient list is displayed), the application navigation module 330 of some embodiments determines that each of these patients may be addressed by a voice command specific to that patient (i.e., the patient's name). Upon making such a determination, the application navigation module 330 creates an entry in the token-function database 340 that corresponds to each new command (i.e., each new patient). In some of these embodiments, each of these entries includes a new token and a corresponding function for the dashboard module 350 to execute. For a patient "John Doe," such an entry could include a new token called SelectJohnDoe( ) and a function that, when executed by the dashboard module 350, selects John Doe in the list of patients.

In some embodiments, the application navigation module 330 performs this creation of entries in the token-function database 340 automatically, without human intervention. As mentioned above, in some embodiments, the application navigation module 330 includes a programmatic interface to the token-function database 340 (e.g., an SQL interface in some embodiments). Through this interface, the application navigation module 330 may modify the token-function database 340 (e.g., through SQL commands in some embodiments) as necessary. In some embodiments, the scripting module 320 performs the modification of the token-function database 340 instead of the application navigation module 330.

Once the token-function database 340 is modified to include the new dashboard function(s), the application navigation module 330 provides the content itself (i.e., the text "John Doe" in this example) and the token (i.e., SelectJohnDoe( ) in this example) to the scripting module 320. The scripting module 320 modifies the text-token database 325 in a similar manner as described above in order to create an entry that correlates the text of the content (i.e., "John Doe" in this example) to the token (i.e., SelectJohnDoe( ) in this example).

As mentioned above, the application navigation module 330 includes an interface with the dashboard module 350 for determining what data is displayed by the dashboard module 350. In some embodiments, when the dashboard module 330 no longer displays the added content, the application navigation module 330 detects that the content is no longer displayed. The application navigation module 330 and the scripting module 320 modify the databases 325 and 340 in a manner similar to that described above in order to remove the new entries, as they no longer correspond to a valid function.

Thus, with the databases 325 and 340 built in such a fashion, a user may select a patient in a patient list simply by speaking the patient's name. In some embodiments, the modules 320 and 330 create a combinatorial voice command. For instance, one part of such a combinatorial voice command would be to speak "select," and a second part of the combinatorial voice command would be to speak the patient's name.

Figure 7:
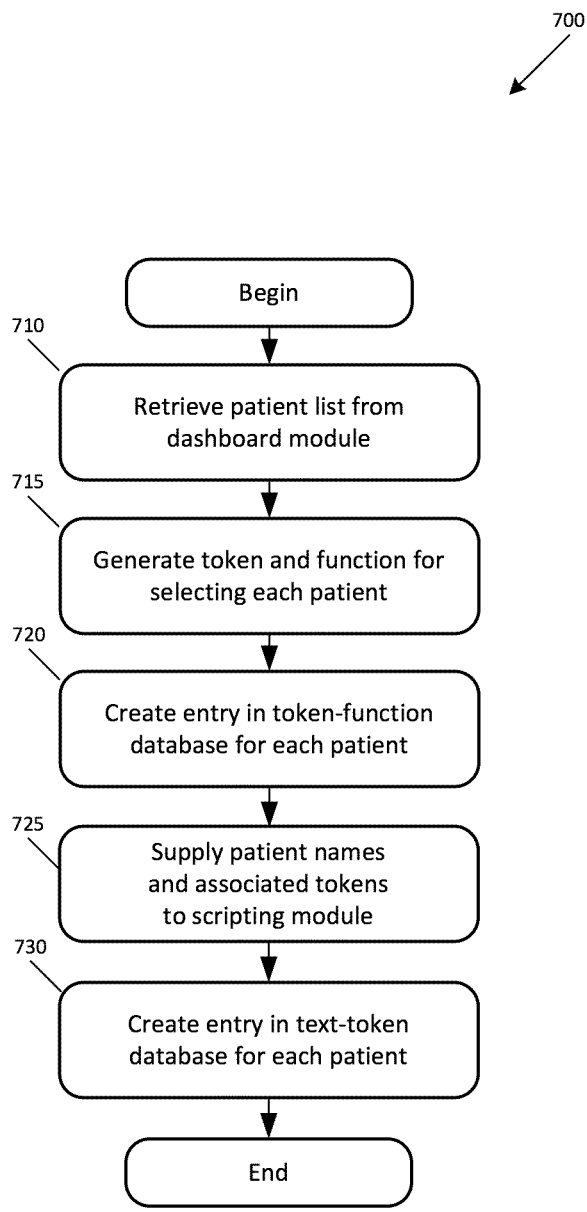
FIG. 7 illustrates a process of some embodiments that creates entries in the text-token database of some embodiments for allowing a user to select a patient by name from a list of patients.

FIG. 7 illustrates an exemplary process 700 that provides the functionality that allows a user to identify a patient in a patient list by name. In some embodiments, the process is performed when a new list (e.g., a list of hospital patients) is displayed in the dashboard module 350 of FIG. 3. The process retrieves (at 710) the list of patient names from the dashboard module 350. The process then generates (at 715) a token and corresponding function (or set of functions) for selecting each patient. As mentioned above, this generating is performed by the application navigation module 330 of some embodiments. The process then creates (at 720) an entry in the token-function database 340 in order to correspond a later-received token to the function (or set of functions) that selects each patient. The process then supplies (at 725) each patient name and its associated token to the scripting module 320. The scripting module 320 then creates (at 730) an entry in the text-token database 325 in order to correspond a later-received recognized text to the associated token.

Once the entry that correlates a patient name to a token is added to the text-token database 325, a user may issue a voice command to select the patient from the list by name. In some embodiments, the data flow of selecting a patient by name is the same as the data flow described above with reference to FIG. 4. Specifically, the scripting module 320 receives recognized text that includes the patient name from the speech recognition module 315, retrieves the token corresponding to the recognized text, and provides the token to the application navigation module 330. The application navigation module 330 retrieves the associated function (or set of functions) that selects the patient from the token-function database 340 and provides the function (or set of functions) to the dashboard module 350 for execution.

E. Macro Voice Commands and Buried Functions

In the examples above, a voice command was described as performing a single dashboard function on a visible control (e.g., operating one user interface tool of a dashboard, such as clicking a single button, selecting a patient from a list, etc.). However, in some embodiments, a voice command performs a "macro," which invokes several dashboard functions (e.g., operates multiple user interface tools of a dashboard, such as clicking several buttons). In some embodiments, a macro invokes a "buried" function. A buried function of some embodiments is a function that is not displayed on the "top level" of the dashboard. A buried function of some embodiments is a function that is not accessible through a single keystroke or "hotkey" combination. A buried function of some embodiments is a function that is necessarily preceded by a series of one or more other functions. In some embodiments, invoking a buried function requires navigation through one or more menus. A buried function is a function that that could be invoked by performing more than one manual operation (e.g., more than one mouse click) in some embodiments.

Some embodiments allow a macro voice command to invoke one or more buried functions, one or more top level functions, or a combination of (1) one or more buried functions and (2) one or more top level functions. For instance, such a macro voice command that includes a combination of buried functions and top level functions may include both (1) a mouse click of a button that is displayed on the GUI and (2) a selection of a menu item within a menu of the GUI.

1. Example Uses of Macro Voice Commands and Buried Functions

Figure 8:
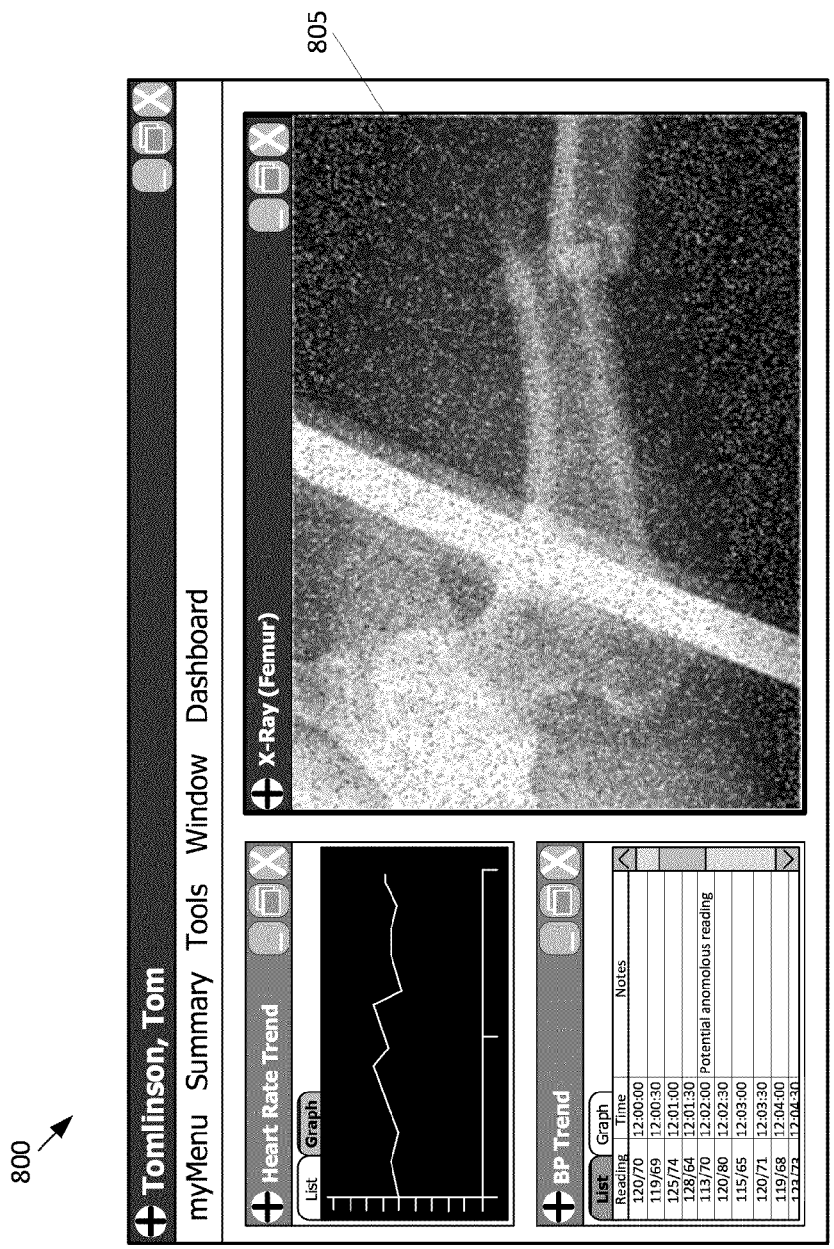
FIGS. 8-15 illustrate examples of dashboard functions (including increasing resolution, zooming, and panning) that would traditionally be executed by multiple mouse clicks, but may instead be executed by initiating a single voice command in some embodiments.

In some embodiments, a voice command invokes a macro, or set of dashboard functions, in a similar process that a voice command invokes a single dashboard function. FIGS. 8-13 illustrate an exemplary series of dashboard functions that would traditionally be executed by multiple mouse clicks, but may instead be executed by initiating a single voice command. FIG. 8 illustrates a dashboard 800. In some embodiments, this dashboard 800 is shown in a GUI similar to the GUI 200 discussed above with reference to FIG. 2, with different modalities.

The dashboard 800 includes an x-ray modality 805, which displays an x-ray image. In some embodiments, the dashboard 800 indicates that this modality 805 is the "active" modality (i.e., the modality on which functions, such as zooming, panning, etc., may be performed). Some embodiments indicate the active state of this modality by drawing a heavy border around the modality, shading the title bar of the modality a different color than the title bars of other modalities of the dashboard, and/or some other way of indicating the active state. The x-ray image shown in the x-ray modality 805 of FIG. 8 is a low-resolution image. Because the image is displayed in low resolution, a user of the dashboard 805 may desire to enhance the image quality (i.e., increase the resolution).

Figure 9:
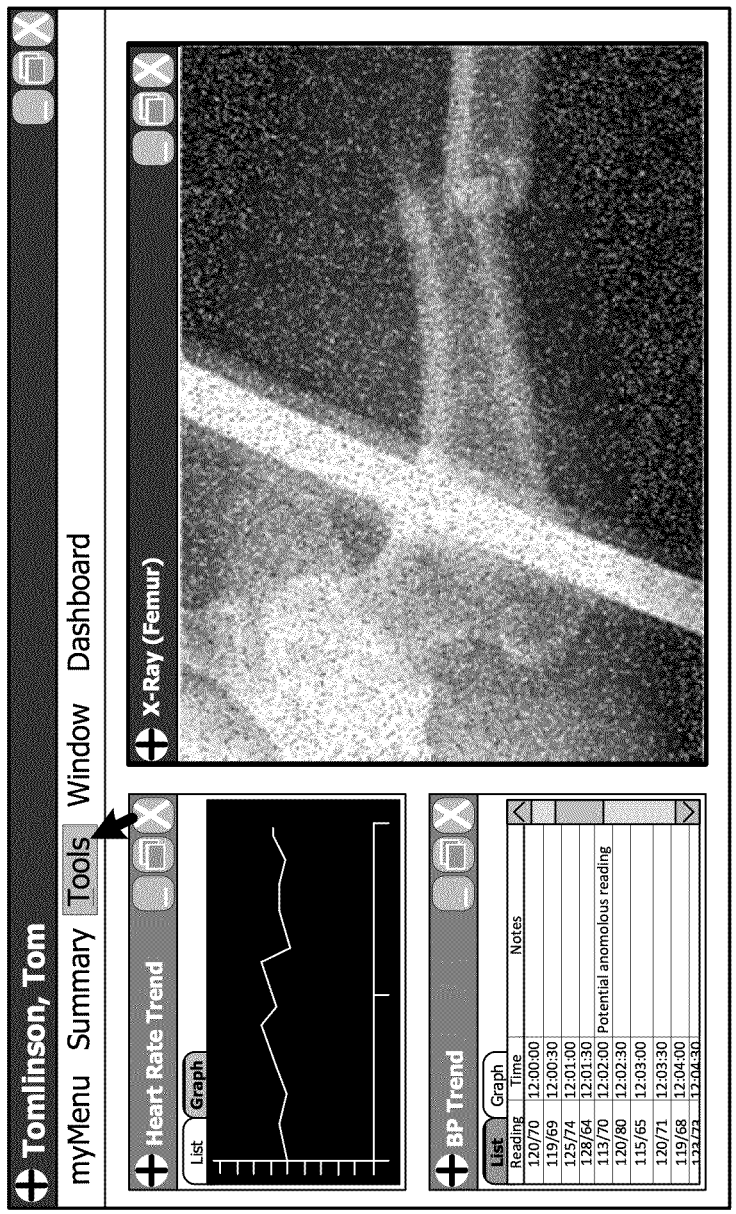
Figure 10:
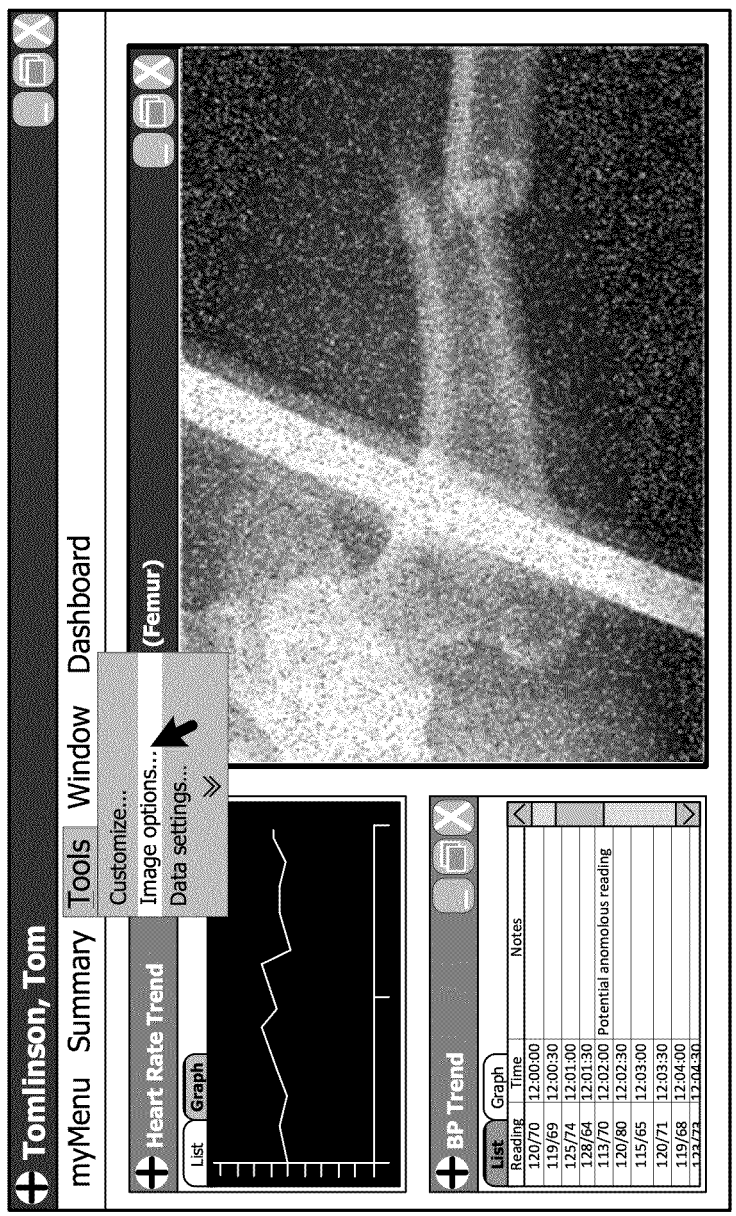

FIGS. 9-12 illustrate a series of functions a user may perform, when the dashboard 800 is controlled by traditional input methods (e.g., mouse, keyboard, etc.). Specifically, these figures show this series of functions being executed through several clicks of a mouse. FIG. 9 illustrates that the user first selects the "Tools" menu. FIG. 10 illustrates that the dashboard then displays the "Tools" menu, from which the user selects the "Image options . . . " menu item.

Figure 11:
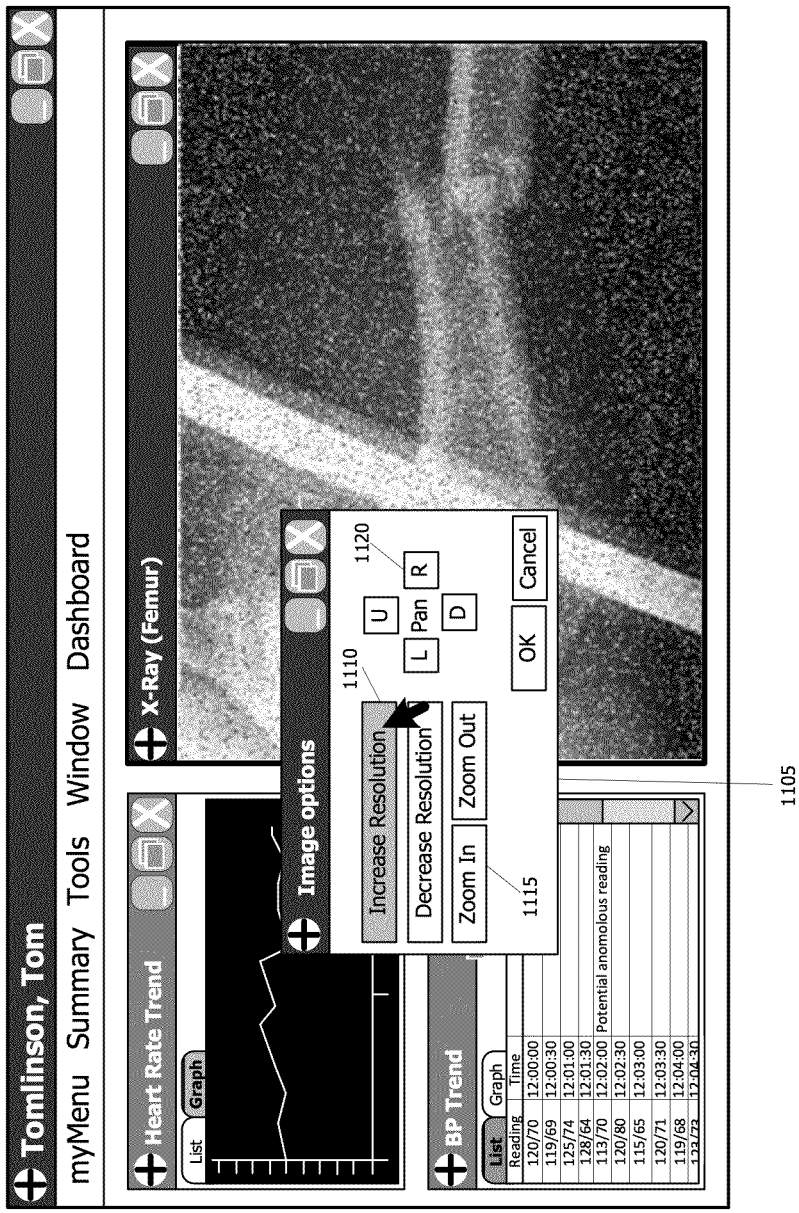
Figure 12:
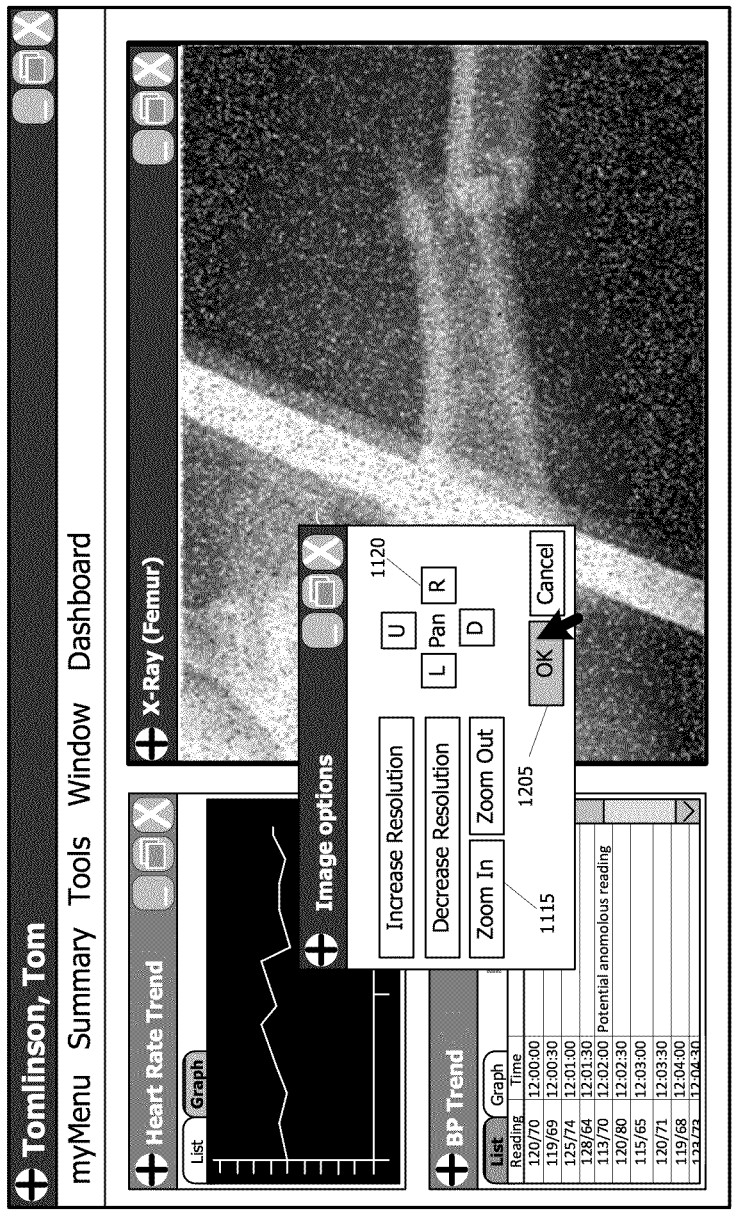
Figure 13:
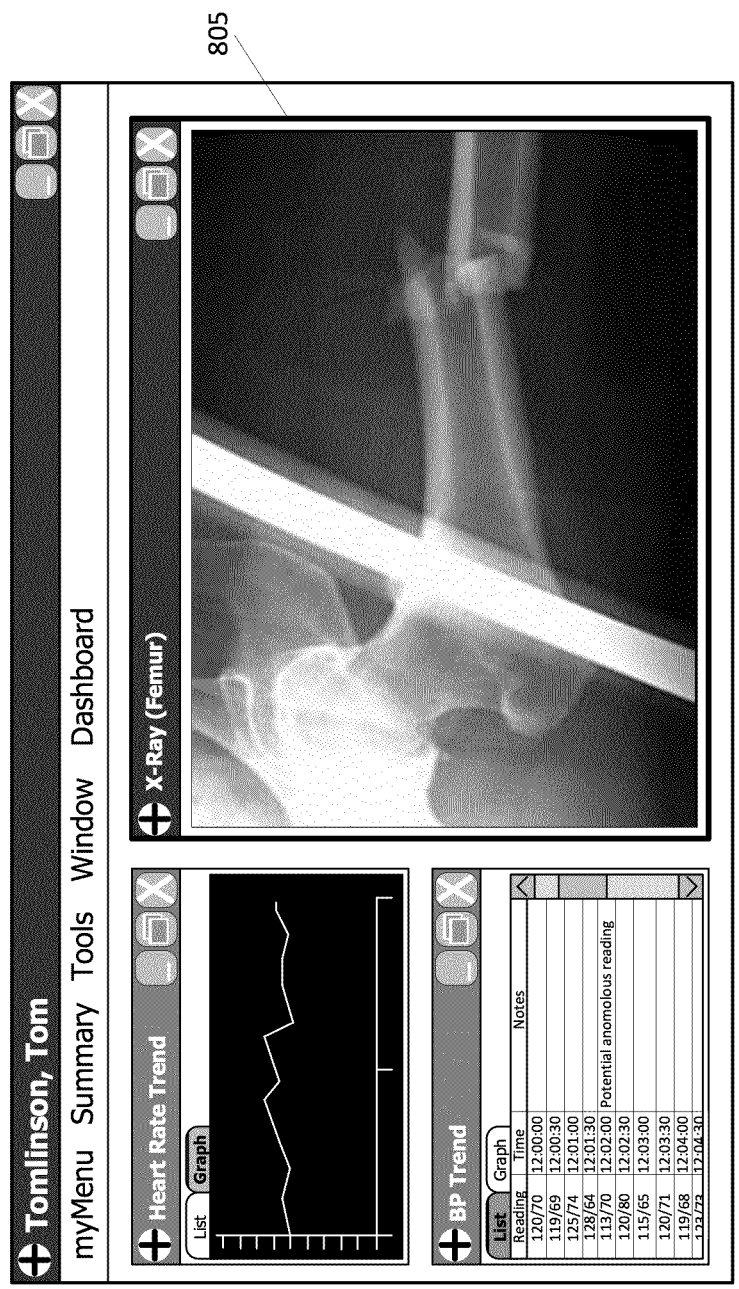

FIG. 11 illustrates that clicking the "Image options . . . " menu item opens an "Image options" dialog box 1105, which displays several operations that may be performed on the image in the active modality (i.e., the x-ray image in the modality 805). In other embodiments, different sets of options, settings, and/or operations may be shown in the dialog box 1105. As shown in FIG. 11, the user clicks the "increase resolution" button 1110 in order to increase the resolution. FIG. 12 illustrates that after clicking the "increase resolution" button, the user clicks the "OK" button 1205. Finally, FIG. 13 illustrates the end result of these multiple functions (i.e., the x-ray modality 805 now displays a higher resolution image than before).

As demonstrated by these figures, increasing the resolution of the x-ray image is a "buried" function, in that the control for increasing the resolution is not displayed on the "top level" of the dashboard, but is rather "buried" within a set of other controls (i.e., a menu and a dialog box in this case). Some embodiments provide a single voice command for executing all of these functions. In other words, using such a voice command would allow a user to transition directly from FIG. 8 to FIG. 13 simply by speaking a single voice command, such as "enhance resolution." In some embodiments, a set of voice commands allow a user to invoke a buried function (e.g., an "enhance resolution" button) by speaking less voice commands than the number of controls that would normally be used to access the buried function.

Figure 14:
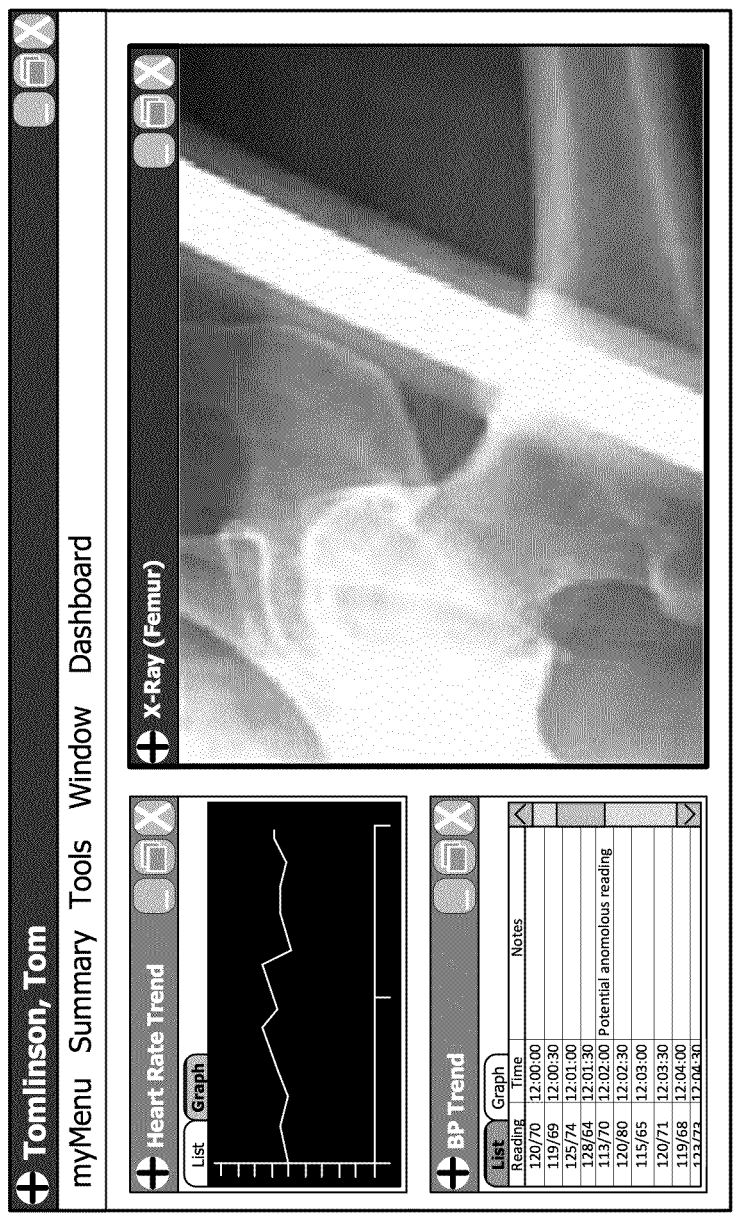

Other examples of buried commands that may be invoked through a single voice command are zooming and panning. FIG. 14 illustrates the end result of a "zoom in" voice command of some embodiments. As shown in FIG. 14, the x-ray shown in FIG. 13 has been zoomed in upon. In some embodiments, the graphical control (e.g., a button) for zooming in is not displayed on the "top level" of the dashboard, but in a menu or submenu that cannot be accessed through a single action of a traditional input method (e.g., a single keystroke, a single mouse click, etc.). In some embodiments, the zoom operation shown in FIG. 14 is invoked by a voice command corresponds to the "zoom in" button 1115 shown in FIGS. 11 and 12. Since a voice command invokes the zooming shown in FIG. 14, operations similar to those illustrated in FIGS. 10-12 (i.e., multiple clicks to access the "zoom in" button 1115) are avoided, thus saving time, effort, and the need to use hands to perform the zooming function.

Figure 15:
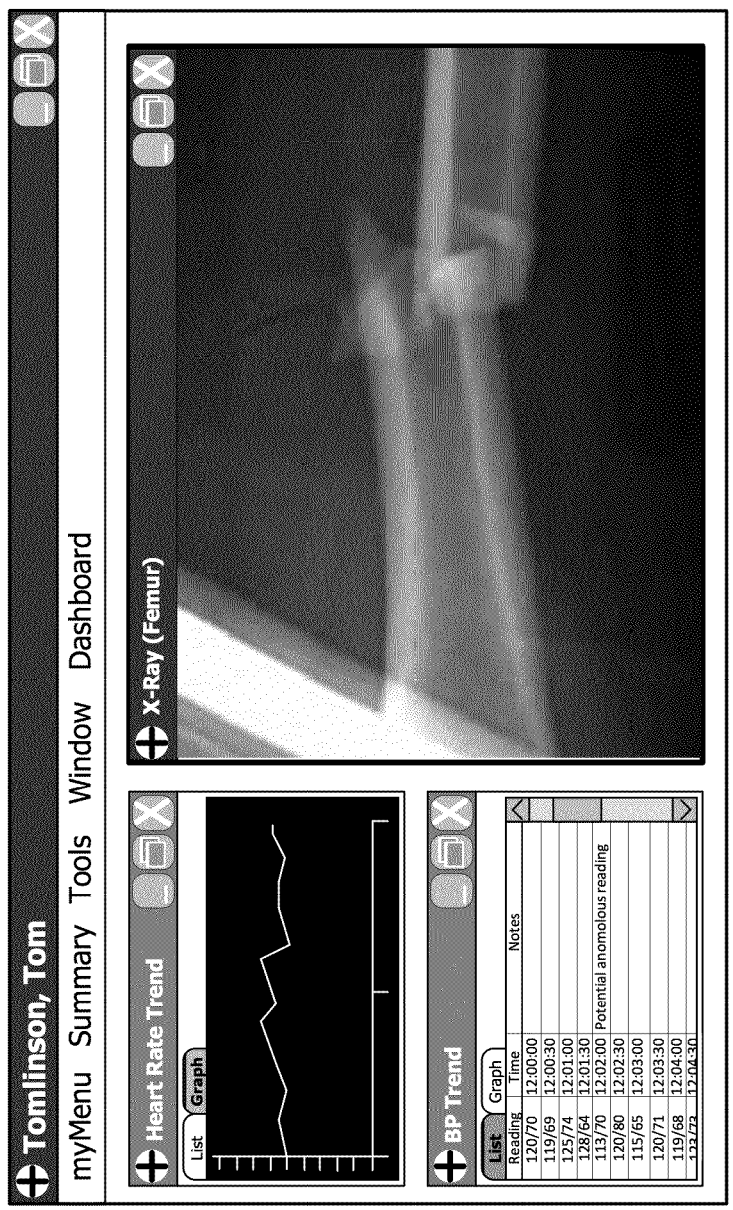

FIG. 15 illustrates an example of the end result of a "pan right" voice command. In this figure, the zoomed x-ray displayed in FIG. 14 has been panned to the right. As with the "increase resolution" and "zoom in" examples discussed above with reference to FIGS. 9-14, the issuance of this single voice command eliminates the need to navigate through multiple graphical controls (i.e., menus, dialog boxes, etc.) to access the buried "pan right" button 1120 shown in FIGS. 11 and 12.

One of ordinary skill in the art would recognize that the above-described examples are provided for illustrative purposes, and do not constitute an exhaustive list of macro voice commands that may be performed. As such, in some embodiments, other macro voice commands may be performed as well. For instance, a first macro voice command may invoke a buried command that opens a modality containing an x-ray image across a first vertical half of a dashboard. A second macro voice command may invoke another buried command that opens another modality containing a set of real-time vital statistics for a patient across a second vertical half of the display interface. In some embodiments, the real-time information is directly retrieved from a set of monitoring equipment that communicably couples to the clinical information dashboard (e.g., from a data source 105, as described above with reference to FIG. 1). In some such embodiments, the clinical information dashboard formats and presents the information acquired from the monitoring equipment to the dashboard without intervening data manipulation devices.

Referring to the previous example, a third voice command may cause the clinical information dashboard to display a set of digitally transcribed notes from an attending physician regarding the patient's current medical condition at the second vertical half of the display interface. Should the user require a better view of the image, the user, through a voice command, invokes a buried function that causes the image to be presented across the entire display interface. Further voice commands may allow the user to zoom into a specific region of the image and manipulate points of interest within the image, after which the user can return the image back into the first vertical half of the display interface.

2. Example Implementation of Macro Voice Command Functionality

In order to perform a macro voice command, the various software modules of some embodiments perform similar functions as described above with reference to FIG. 4. Briefly, the scripting module 320 of FIG. 4 correlates recognized text of a voice command to a token and supplies the token to the application navigation module 330. The application navigation module 330 checks whether the token has a corresponding entry in the token-function database 340. When the voice command corresponds to multiple functions, the token-function database 340 of some embodiments corresponds multiple dashboard functions to a token. Once the multiple functions are retrieved from the token-function database 340, the application navigation module 330 provides these functions to the dashboard module 350 for execution.

Figure 16:
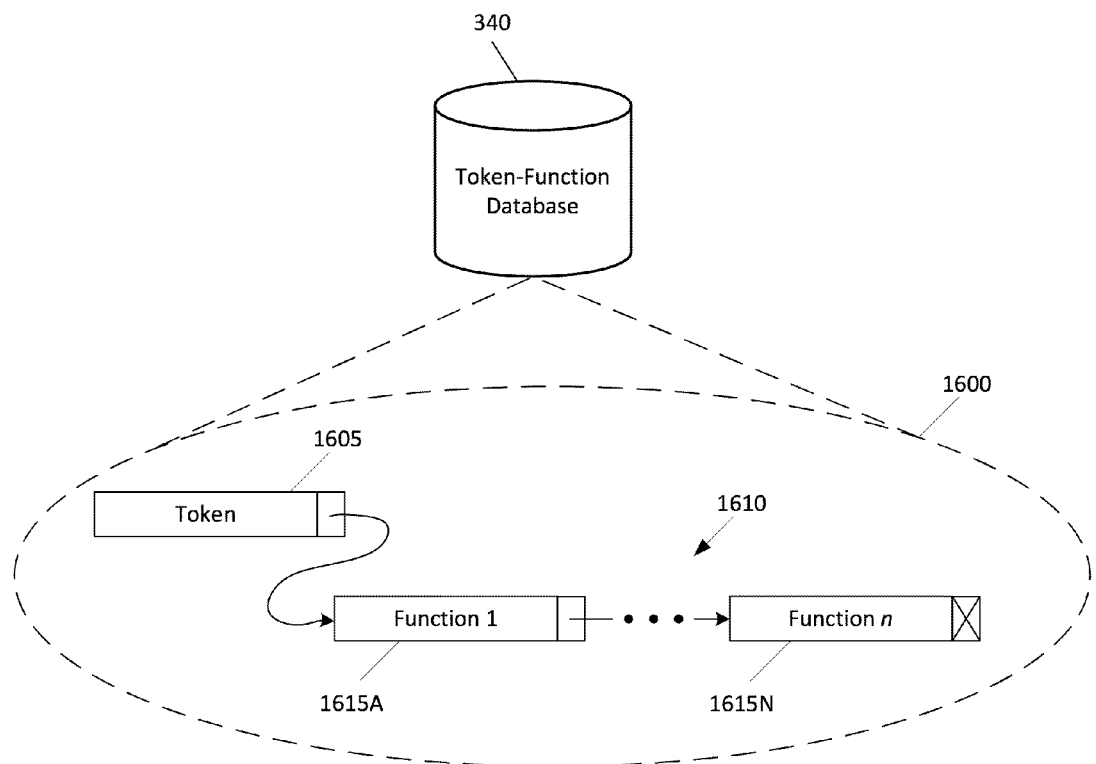
FIG. 16 conceptually illustrates an example of a data structure of a token-function database of some embodiments.

FIG. 16 illustrates a linked list data structure that the token-function database 340 uses in some embodiments. In this figure, exploded view 1600 conceptually illustrates such a linked list data structure that correlates a token 1605 with a set of dashboard functions 1615A-1615N. In some of these embodiments, a token 1605 is associated with a conceptual pointer that points to a linked list 1610 of dashboard functions 1615A-1615N. In some embodiments, this linked list includes n dashboard functions 1615, where n is any number.

While a specific example of organization of the token-function database 340 was described above with reference to FIG. 16, one of ordinary skill in the art would recognize that other implementations are possible. For instance, some embodiments use multiple relational tables to correlate a token to multiple functions. In some embodiments, the token-function database 340 includes data that indicates the order in which the multiple functions are to be performed.

F. Overloaded Dashboard Functions

Figure 17:
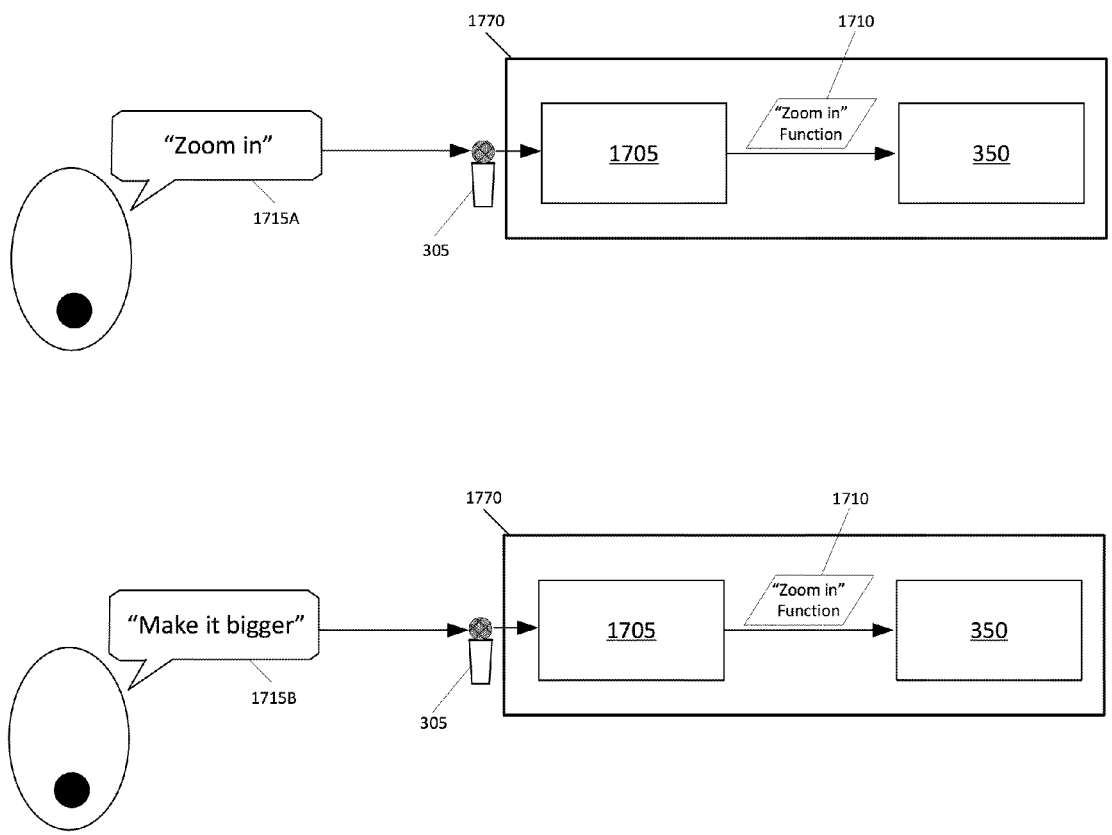
FIG. 17 illustrates overloaded dashboard function capabilities of some embodiments.

In some embodiments, a single dashboard function can be initiated by multiple different voice commands. Such a function that is associated with multiple different voice commands is referred to as an "overloaded" function. An overloaded function allows multiple users to use the same voice control dashboard without loading new settings for a user. For instance, two or more healthcare providers (e.g., doctors, surgeons, nurses, etc.) may use the same voice control dashboard at the same time, where each of the healthcare providers prefers different voice commands for the same dashboard function. FIG. 17 illustrates an example of such an overloaded function. This figure shows a computing device 1770 of some embodiments at two different times. In some embodiments, the computing device 1770 that runs a set of software modules 1705 and a dashboard module 350 is an example of the computing device 370 of some embodiments, as shown in FIG. 3.

The computing device 1770 is attached to a speech input device 305 (e.g., a microphone), which receives speech 1715 and provides the received speech 1715 to the set of software modules 1705. In some embodiments, the set of software modules 1705 conceptually includes the speech recognition module 315, the scripting module 320, the text-token database 325, the application navigation module 330, and the token-function database 340 shown in FIG. 3. In some embodiments, the set of software modules 1705 performs the same functionality as the software modules 315, 320, and 330 and databases 325 and 340 of FIG. 3. Specifically, in some embodiments, the set of software modules 1705 receives speech and provides the dashboard module 350 with a function (or set of functions) to execute, based on the received speech.

In FIG. 17, two users issue different voice commands 1715A and 1715B at different times. The first voice command 1715A is "zoom in," while the second voice command 1715B is "make it bigger." As shown in FIG. 17, both voice commands 1715A and 1715B cause the set of software modules 1705 to provide the same function (i.e., a "zoom in" function 1710) to the dashboard module 350 for execution by the dashboard module 350. Thus, the "zoom in" function 1710 is an overloaded function, as multiple voice commands invoke this function.

Figure 18:
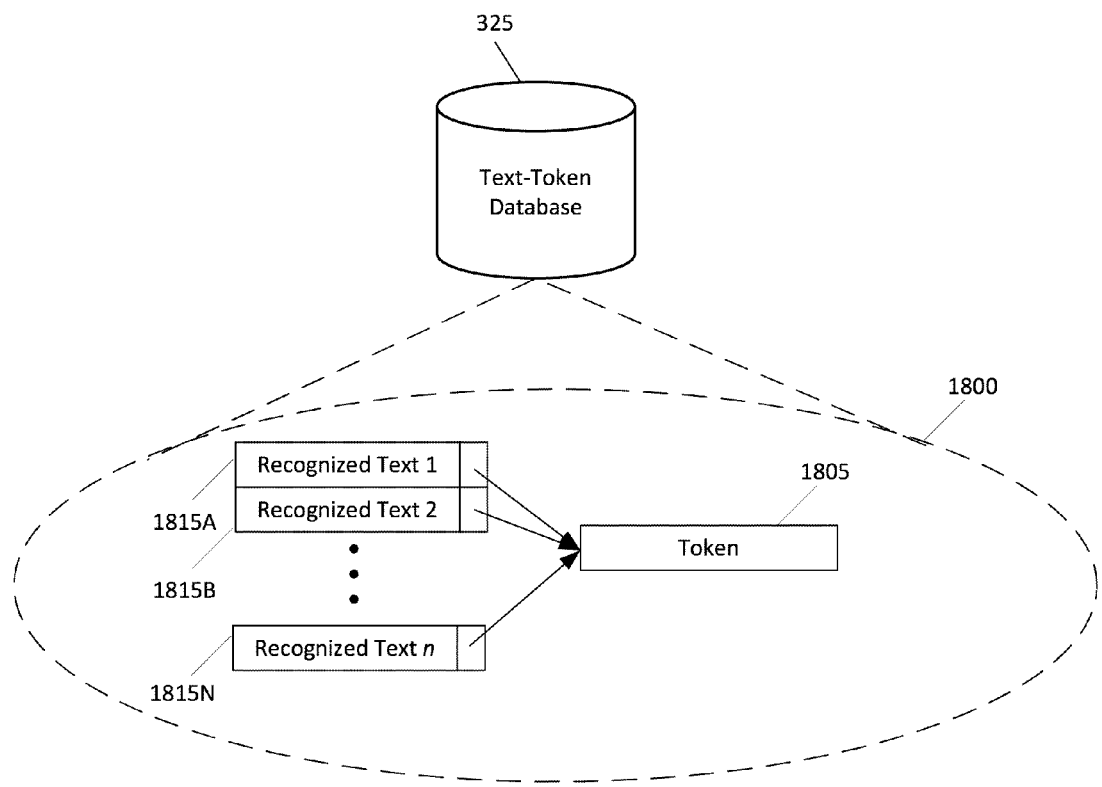
FIG. 18 conceptually illustrates an example of a data structure of a text-token database of some embodiments.

In order to achieve overloaded dashboard functionality, some embodiments correlate multiple recognized texts to a single token in the text-token database 325 using pointers. FIG. 18 conceptually illustrates the data structure of the text-token database 325 of some embodiments. In this figure, exploded view 1800 conceptually illustrates a set of n recognized texts 1815A-1815N, where n is any number. Each of these recognized texts 1815 includes a pointer to a single token 1805, thus indicating that the recognized texts 1815 each correlate to the token 1805. Thus, in this example, the token 1805 is associated with n recognized texts 1815A-1815N.

While a specific conceptual example of organization of the text-token database 325 was described above with reference to FIG. 18, one of ordinary skill in the art would recognize that various implementations are possible. For instance, some embodiments use multiple relational tables to correlate a token to multiple recognized texts. Moreover, one of ordinary skill would recognize that other recognized texts and other tokens may, although not shown in the figure, may be present in the text-token database 325.

While the above-described embodiments mention overloaded functions in the context of a single dashboard function being correlated to multiple voice commands, one of ordinary skill in the art would recognize that other combinations of other embodiments of the invention are possible. For example, a set of functions (e.g., a macro voice command), as described above, may be associated with multiple voice commands. In such an example, the macro voice command "increase resolution" could be associated with the voice commands "increase resolution" and "enhance resolution."

G. Text-to-Speech Mode

In some embodiments, text displayed in a dashboard may be read aloud to a user via text-to-speech functionality. FIG. 19 conceptually illustrates a data flow of some embodiments that provide such text-to-speech functionality. FIG. 19 shows the interface 300 of some embodiments, described above with reference to FIG. 3. In order to command the interface 300 to read dashboard text aloud, a user issues a voice command (e.g., "read"). In some embodiments, before the user issues the "read" voice command, the user previously selects the text to be read. This selection can occur through a previous command (e.g., a previous voice command, a mouse click, a default selection when opening a page, etc.).

The speech input device 305 receives this voice command and provides the voice command to the speech recognition module 315. The speech recognition module 315 converts the speech into recognized text, "read." The speech recognition module 315 provides this recognized text to the scripting module 320, which checks the text-token database 325 for a corresponding token. Upon finding the corresponding token that indicates that the user desires to listen to a spoken version of displayed text, the scripting module 320 enters "text-to-speech mode."

The scripting module 320 then provides the token to the application navigation module 330. In some embodiments, this token is a text-to-speech token that indicates that the scripting module 320 is in text-to-speech mode. The application navigation module 330 of some embodiments recognizes this token as a text-to-speech token indicating that the scripting module 320 is in text-to-speech mode. In response to this text-to-speech token, the application navigation module 330 of some embodiments does not consult the token-function database 340 to find a corresponding function for the dashboard. In some embodiments, the application navigation module 330 uses the text-to-speech token as a command for the application navigation module 330 itself instead of using the token to find a correlating function in the token-function database 340.

As mentioned above, the application navigation module 330 of some embodiments, through its interface with the dashboard module 350, is aware of (or "knows") the content displayed by the dashboard module 350. In some embodiments, this content is retrieved from a data storage (not shown) that stores the data displayed by the dashboard module 350. The application navigation module 330 of some embodiments further knows what content is selected in the dashboard module 350. Thus, upon receiving the "read" text-to-speech token, the application navigation module 330 knows precisely what text the user wishes to be read. After receiving the "read" text-to-speech token, the application navigation module 330 provides the requested text to the scripting module 320. In some embodiments, after the application navigation module 330 provides the requested text, the application navigation module 330 indicates (e.g., appends an annotation to the end of the text) to the scripting module 320 that there is no more text to read aloud.

As mentioned above, in this figure, the scripting module 320 is in text-to-speech mode. In text-to-speech mode, when receiving text from the application navigation module 330, the scripting module 320 provides the received text to the text-to-speech module 335 that converts this text to converted speech. In some embodiments, this text-to-speech module 335 may be an "off-the-shelf" software component (e.g., TextAloud by NextUp Technologies, or any other text-to-speech module). The text-to-speech module 335 of some embodiments interfaces (e.g., through a set of drivers) with the audio output device 345. Through the interface, the converted speech is played back through the audio output device 345.

Although not shown in the figure, other data flows are possible in order to achieve the same, or similar, functionality in some embodiments. For instance, the application navigation module 330 may include an interface to the text-to-speech module 335 in some embodiments. In some embodiments, the dashboard module 350 itself includes text-to-speech functionality, and thus directly interfaces with the audio output device 345. In some embodiments, the functionality of audibly outputting content displayed in the dashboard module 350 does not require speech input. In other words, some embodiments allow a user to invoke the text-to-speech functionality through traditional manual input commands (e.g., mouse, keyboard, etc.).

H. Data Input Mode

As mentioned above, dashboards of some embodiments can be used not only for displaying (or outputting) data, but for inputting data as well. In some embodiments, the data input into a dashboard is provided to a clinical data manager 110, shown in FIG. 1, in order to store the data in one or more centralized databases (e.g., the dashboard database 120). In some embodiments, a user may enter data into a voice-controlled dashboard by using voice dictation.

Figure 20:
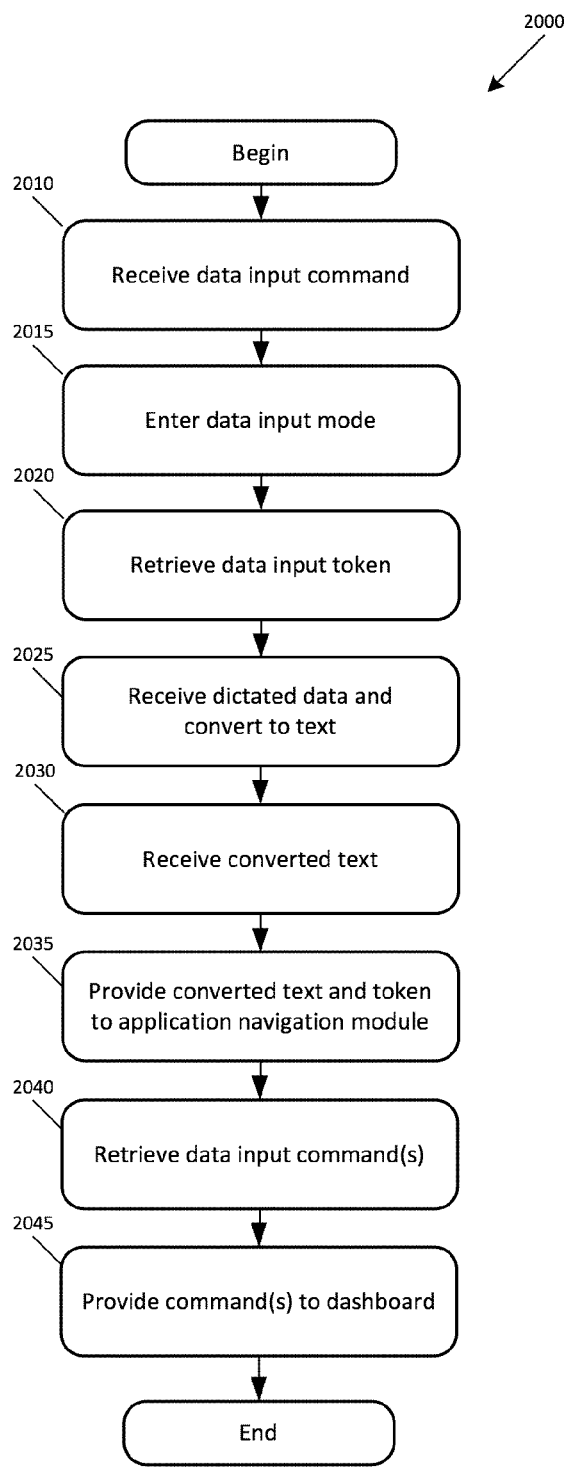
FIG. 20 illustrates a process by which data may be input by speech into a dashboard.

FIG. 20 illustrates a process 2000 of some embodiments that allows a user to enter data into the dashboard using voice dictation. In some embodiments, the software modules of an interface 300 perform the process 2000. The process receives (at 2010) a command that indicates that the user wishes to enter data using voice dictation. In some embodiments, this command is received by the scripting module 320 shown in FIG. 3. In some embodiments, this command itself is a voice command, such as "enter data," provided to the scripting module as recognized text. Upon receiving this command, the process enters (at 2015) the scripting module 320 into data input mode.

Once the scripting module 320 is in data input mode, the process retrieves a data input mode token. In some embodiments, this token is retrieved by the scripting module 320. In some of these embodiments, the scripting module 320 retrieves this token from the text-token database 325. In some embodiments, this token is not retrieved from the text-token database 325, but is instead previously "hardcoded" into the scripting module 325 by a programmer of the scripting module 325.

The process then receives (at 2025) dictated data and converts the dictated data into recognized text. In some embodiments, the speech recognition module 315, as shown in FIG. 3, performs this receiving and converting. The process then receives (at 2030) the recognized text. In some embodiments, the scripting module 320 receives this recognized text. The process provides (at 2035) the recognized text and the previously retrieved input mode token to the application navigation module 330, shown in FIG. 3.

The process then retrieves (at 2040) a dashboard function that corresponds to the retrieved token. In some embodiments, the application navigation module 330 receives this dashboard function from the token-function database 340. In some embodiments, the application navigation module 330 retrieves multiple dashboard functions for the input mode token and the recognized text.

These multiple dashboard functions may each correspond to a keystroke of a single letter of the text. For instance, if a user wishes to input a first name, "John," into the dashboard, the application navigation module 330 of some embodiments would receive the text "John" and a token indicating data input. The application navigation module 330 would then retrieve one command four times, each with a different parameter corresponding to a different letter of the word: KeyStroke('J'), KeyStroke('o'), KeyStroke('h'), and Keystroke('n'). In some embodiments, other functions are possible (e.g., a single function that inputs a full word or multiple words) in order to achieve the same result.

The process then provides (at 2045) the command(s) to the dashboard module 350, shown in FIG. 3. In response to receiving this command (or set of commands), the dashboard module 350 inputs the received data. In some embodiments (e.g., when keystroke commands are provided to the dashboard module 350), this data input is handled as keystrokes of a keyboard would be handled. In some embodiments, this data is subsequently provided to an external location (e.g., clinical data manager 110) through a network 130 (e.g., a LAN, the Internet, or some other type of network) so that it can be viewed by other dashboards, and/or by the same dashboard at a later time.

I. Voice-Controlled Dashboard in a Sterile Environment

Figure 21:
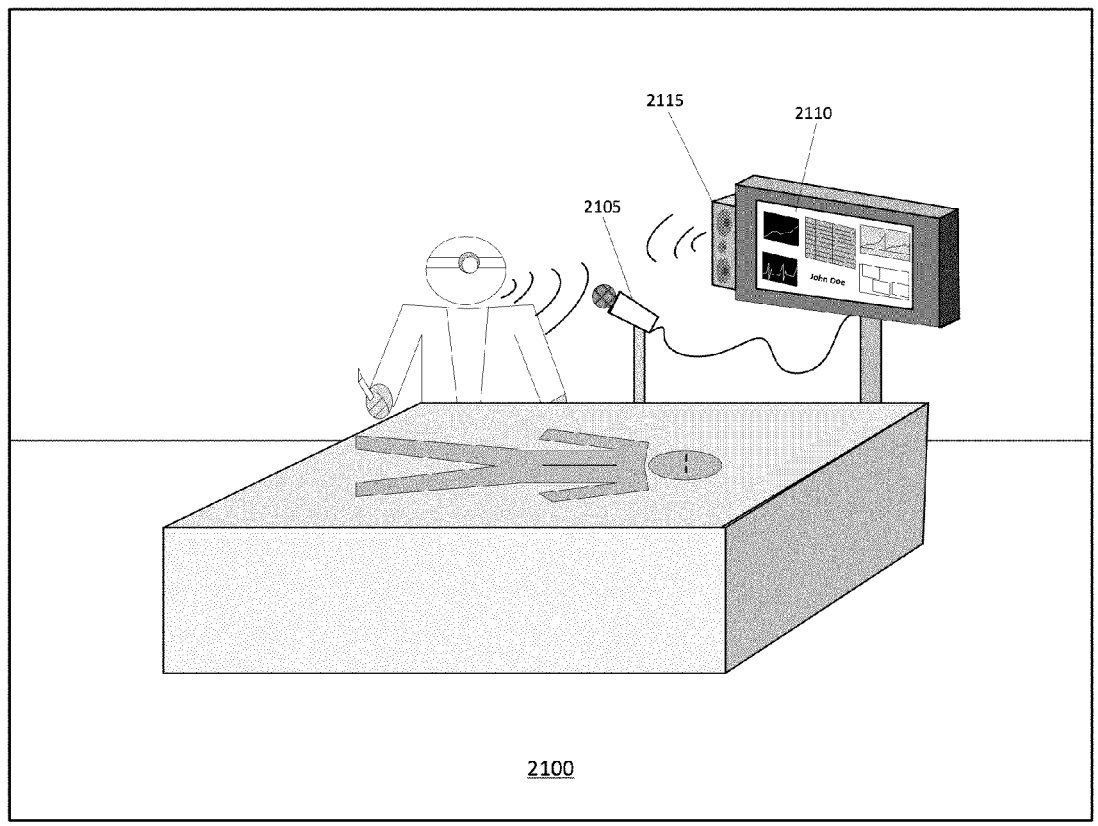
FIG. 21 illustrates a sterile environment in which some embodiments of the invention may be used.

FIG. 21 illustrates a voice-controlled clinical information dashboard 2110 of some embodiments used in a sterile environment 2100 (e.g., an operating room, an intensive care unit, etc.). FIG. 21 also shows an audio input device 2105 (e.g., a microphone) and an audio output device 2115 (e.g., a speaker or a set of speakers).

In this figure, a surgeon performs surgery on a patient in the sterile environment 2100 while the voice-controlled clinical information dashboard 2110 displays clinical information (e.g., vital signs, lab results, etc.) in multiple windows (or "modalities"). The surgeon controls the voice-controlled clinical information dashboard 2110 (e.g., manipulates which information is displayed, inputs data, etc.) through voice commands. The voice commands are received by the audio input device 2105, which is communicatively coupled to a computer system (not shown) on which the clinical information dashboard 2110 runs.

In some embodiments, the audio output device 2115 outputs audio from the clinical dashboard 2110. This audio may include a spoken version of text and/or other data displayed by the clinical dashboard 2110. When used in a sterile environment, the voice-controlled clinical information dashboard 2110 eliminates the need for a user to compromise the sterile environment by "de-gowning" or "de-gloving" in order to control the dashboard through a traditional input mechanism (e.g., mice, keyboards, touch screens, scroll wheels, trackpads, etc.).

J. Example Voice Commands

In the preceding discussion, several different exemplary voice commands were discussed. However, one of ordinary skill in the art would recognize that many other voice commands may be used. Table 1, below, illustrates more examples of voice commands that may be used to invoke dashboard functions. As with the abovementioned examples, the examples in the table are provided merely for illustrative purposes, and other commands may be used in some embodiments.

TABLE 1

| Voice Command | Dashboard function(s) |
|---|---|
| COMMANDS | Display list of available voice commands |
| LAUNCH ICIS | Launch dashboard |
| GCQ | Launch dashboard |
| ICIS | Launch dashboard |
| LOGIN | Log into dashboard |
| PASSWORD | Select "password" field of login screen |
| DOCTOR NAME | Select "doctor name" field of login screen |
| TAB | "Tab" keystroke |
| ENTER | "Enter" keystroke |

TABLE 1-continued

| Voice Command | Dashboard function(s) |
|---|---|
| O R CAMERAS | Maximize window(s) containing all feeds to a set of cameras within a set of operating rooms |
| O R FIFTEEN | Bring to focus particular camera within particular operating room |
| HELP | Open "help" window. |
| REPORTS | Open window displaying reports. |
| LABS | Open window displaying lab results. |
| SCANS | Open window displaying scans. |
| VITALS | Open window displaying vital statistics. |
| DEMOGRAPHICS | Open window displaying demographic information. |
| STATUS | Open window displaying status. |
| FIND | Find specific patient or multiple patients. |
| LOCATION_WESTWOOD | Search parameter. |
| SEVEN WEST I C U | Search parameter. |
| SIX EAST I C U | Search parameter. |
| BACK | "Back" button of dashboard. |
| ADD ALL TO QUICK LIST | Sort results of a search. |
| FIND ALL PATIENTS IN I C U | Retrieve file and associated information for all patients currently located in ICU. |
| TOP | Navigate through search results, modalities, icons, or other objects. |
| BOTTOM | Navigate through search results, modalities, icons, or other objects. |
| HIGHER | Navigate through search results, modalities, icons, or other objects. |
| LOWER | Navigate through search results, modalities, icons, or other objects. |
| TILE | Display all modalities as "tiles" in dashboard. |
| WINDOW | Select particular modality. |
| HORIZONTAL | Tile horizontally. |
| VERTICAL | Tile vertically. |
| GO | Choose modality or other data object for focus. |
| SKIP DOWN | Navigate through modalities. |
| MINIMIZE | Minimize modality or dashboard. |
| MAXIMIZE | Maximize modality or dashboard. |
| TOGGLE | Toggle a control of the dashboard. |
| MY MENU | Select menu called "My Menu" |
| MENU NAME | Begin dictation of a menu name. |
| LEFT | "Left" keystroke. |
| RIGHT | "Right" keystroke. |
| NEXT | Select next modality in sequence. |
| HIDE GCQ | Hide modality. |
| SHOW GCQ | Show modality. |
| CANCEL | "Cancel" button of dashboard. |
| UP | "Up" keystroke. |
| DOWN | "Down" keystroke. |
| DASH FOUR | Select a dashboard named "four." |
| LEVEL | Adjust look and feel by adjusting level. |
| SOFTER | Adjust look and feel by increasing softness. |
| SHARPER | Adjust look and feel by increasing sharpness. |
| BRIGHTER | Adjust look and feel by increasing brightness. |
| DARKER | Adjust look and feel by increasing darkness. |
| RADIOLOGY REPORT | Display radiology report modality. |
| LIST SCANS | Display list of scans. |
| THUMBS | Display thumbnails of images. |
| INVERT | Invert organization of thumbnail. |
| IMAGES | Identify an image. |
| CLICK | Mouse click. |
| DOUBLE CLICK | Mouse double-click. |
| FOCUS | Select modality for focus. |
| SELECT | Select modality for focus. |
| IMAGE ELEVEN | Select image eleven. |
| MORE THUMBS | Display more thumbnail images. |
| LESS THUMBS | Display less thumbnail images. |
| ZOOM ELEVEN | Select image eleven and zoom. |
| ZOOM IN | Zoom in on selected image. |
| ZOOM OUT | Zoom out on selected image. |
| BIGGER | Zoom in on selected image. |
| SMALLER | Zoom out on selected image. |
| PAN | Pan selected image. |
| EAST | Pan selected image right. |
| WEST | Pan selected image left. |
| UNDO | "Undo" function of dashboard. |
| FIRST | Select first item within modality. |
| ONE | Select first item within modality. |
| SECOND | Select second item within modality. |
| THIRD | Select third item within modality. |
| DESCRIPTION | Toggle text object associated with an image. |

TABLE 1-continued

| Voice Command | Dashboard function(s) |
|---|---|
| MESSAGE | Send message to user, file, or other entity. |
| ATTENDING | Select attending physician. |
| PATIENT | Select patient. |
| BONE | Manipulate information within demographics tab. |
| BRAIN | Manipulate information within demographics tab. |
| ORIGINAL | Manipulate information within demographics tab. |
| EXIT | Close dashboard or modality. |
| GOODBY G C Q | Close dashboard or modality. |
| CLOSE | Close dashboard or modality. |
| DELETE | Close dashboard or modality. |

IV. Computer System

Figure 22:
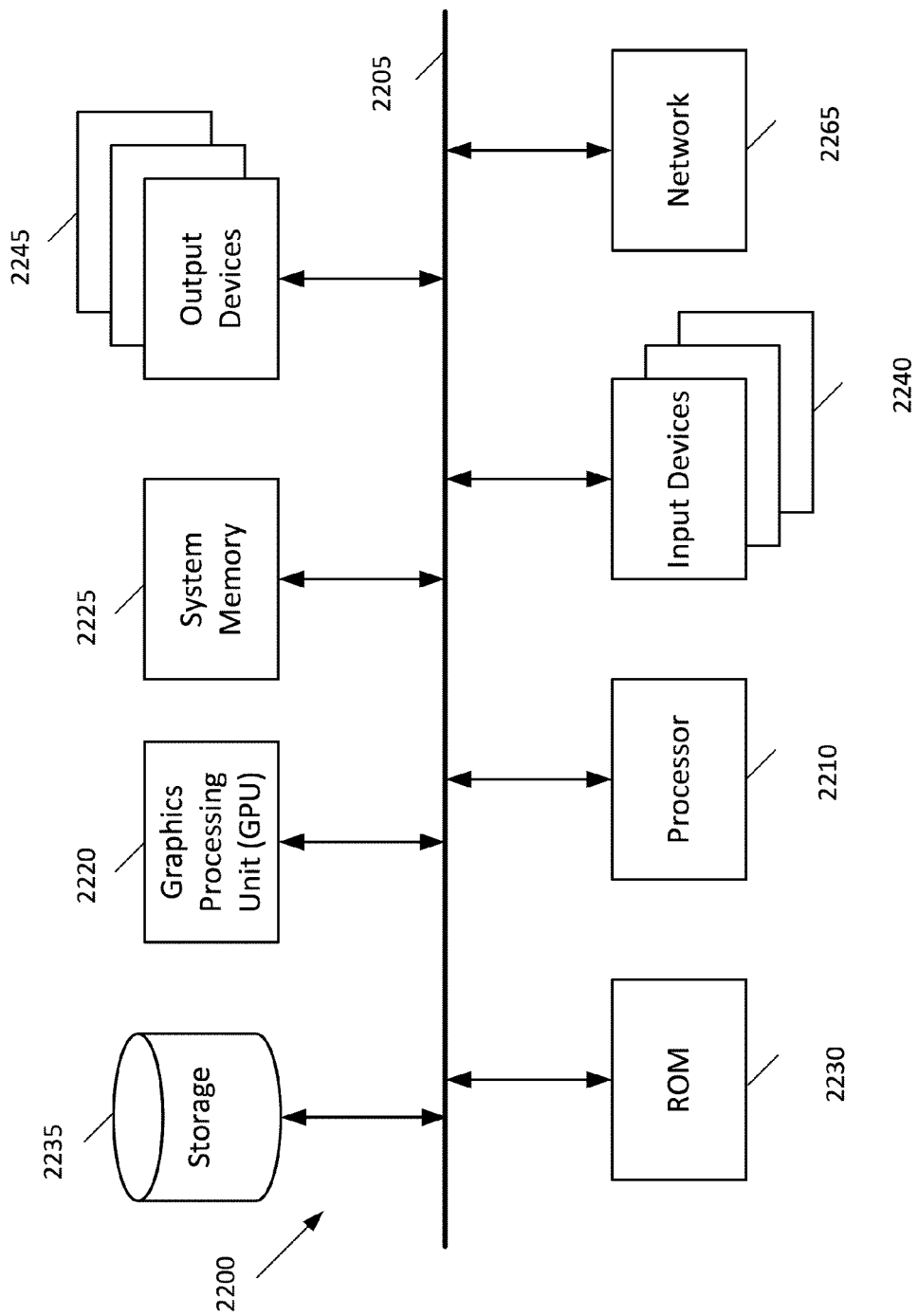
FIG. 22 illustrates a computer system in which some embodiments of the invention may be used.

FIG. 22 illustrates a computer system 2200 with which some embodiments of the invention are implemented. For instance, in some embodiments, the computing device 370 illustrated in FIGS. 3, 4, and 6 are implemented as the computer system 2200. In some embodiments, the computer system 2200 includes various types of computer readable media and interfaces for various other types of computer readable media. Computer system 2200 includes a bus 2205, a processor 2210, a graphics processing unit ("GPU") 2220, a system memory 2225, a read-only memory ("ROM") 2230, a permanent storage device 2235, input devices 2240, and output devices 2245.

The bus 2205 collectively represents all system, peripheral, and chipset buses that communicatively connect the numerous internal devices of the computer system 2200. For instance, the bus 2205 communicatively connects the processor 2210 with the read-only memory 2230, the GPU 2220, the system memory 2225, and the permanent storage device 2235.

From these various memory units, the processor 2210 retrieves instructions to execute and data to process in order to execute the processes of the invention. Some instructions are passed to and executed by the GPU 2220. In some embodiments, the GPU 2220 can offload various computations or complement the image processing provided by the processor 2210.

The ROM 2230 stores static data and instructions that are used by the processor 2210 and other modules of the computer system. The permanent storage device 2235, on the other hand, is a read-and-write memory device. This device is a non-volatile memory unit that stores instructions and data even when the computer system 2200 is off. Some embodiments of the invention use a mass-storage device (such as a magnetic or optical disk and its corresponding disk drive) as the permanent storage device 2235.

Other embodiments use a removable storage device (such as a floppy disk, flash drive, or iOmega Zip® disk, and its corresponding disk drive) as the permanent storage device. Like the permanent storage device 2235, the system memory 2225 is a read-and-write memory device. However, unlike storage device 2235, the system memory is a volatile read-and-write memory, such a random access memory ("RAM"). The system memory stores some of the instructions and data that the processor needs at runtime. In some embodiments, the invention's processes are stored in the system memory 2225, the permanent storage device 2235, and/or the read-only memory 2230.

The bus 2205 also connects to the input and output devices 2240 and 2245. The input devices enable the user to communicate information and select commands to the computer system. In some embodiments, the input devices 2240 include alphanumeric keyboards and pointing devices (also called "cursor control devices"). In some embodiments, the input devices 2240 also include audio input devices (e.g., microphones, midi musical instruments, etc.). The output devices 2245 display images generated by the computer system. For instance, these devices display a GUI. The output devices include printers and display devices, such as cathode ray tubes ("CRT") or liquid crystal displays ("LCD").

In some embodiments, the computer system 2200 includes a set of hardware input/output ("I/O") ports (not shown) through which the input devices 2240 (e.g., a microphone) and output devices 2245 (e.g., a display device) supply and receive data. In some embodiments, this set of I/O ports includes an audio input port, such as a one-quarter or one-eighth inch port (or "jack"). In some embodiments, the set of I/O ports includes an audio output port, such as one or more one-quarter or one-eighth inch jacks. In some embodiments, one or both of these audio I/O ports include a wireless interface, such as radio frequency ("RF"), Bluetooth, or some other wireless interface. In some embodiments, the set of I/O ports includes a video output port (e.g., VGA, DVI, S-video etc.). Furthermore, the computer system 2200 may have other I/O ports not specifically enumerated or shown in the figure (e.g., USB ports, PS/2 ports, serial ports, etc.) for other input and/or output devices.

Finally, as shown in FIG. 22, bus 2205 also couples computer 2200 to a network 2265 through a network adapter (not shown). In this manner, the computer can be a part of a network of computers (such as a LAN, WAN, an intranet, or a network of networks, such as the Internet). For example, the computer 2200 may be coupled to a web server (through network 2265) so that a web browser executing on the computer 2200 can interact with the web server as a user interacts with a GUI that operates in the web browser.

Any or all components of computer system 2200 may be used in conjunction with the invention. For instance, in some embodiments, the rendering of the dashboards of some embodiments is performed by the GPU 2220 instead of the CPU 2210. Similarly, other image display functions can be offloaded to the GPU 2220 where they are executed before the results are passed back into memory or the processor 2210. However, a common limitation of the GPU 2220 is the number of instructions that the GPU 2220 is able to store and process at any given time. Therefore, some embodiments adapt instructions for implementing processes so that these processes fit onto the instruction buffer of the GPU 2220 for execution locally on the GPU 2220. Additionally, some GPUs 2220 do not have sufficient processing resources to execute the processes of some embodiments, and therefore the CPU 2210 executes the instructions. One of ordinary skill in the art would appreciate that any other system configuration may also be used in conjunction with the present invention.

As mentioned above, the computer system 2200 may include one or more of a variety of different computer-readable media. Some examples of such computer-readable media include tangible computer-readable media, such as RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, Iomega Zip® disks, read-only and recordable blu-ray discs, any other optical or magnetic media, and/or floppy disks.

While the invention has been described with reference to numerous specific details, one of ordinary skill in the art will recognize that the invention can be embodied in other specific forms without departing from the spirit of the invention. Thus, one of ordinary skill in the art would understand that the invention is not to be limited by the foregoing illustrative details, but rather is to be defined by the appended claims.

We claim:

1. A method for controlling clinical data in a medical computer system having a display, comprising:
    displaying a first set of clinical data from at least one clinical database in a first set of windows on the display, the display having a plurality of controls for performing a plurality of functions;
    generating a subset of available voice commands based upon the first set of clinical data displayed in the first set of windows from a set of voice commands stored in at least one voice command database, the subset of available voice commands having fewer voice commands than the set of voice commands;
    receiving at least one new item of clinical data;
    displaying said at least one new item of clinical data in the first set of windows;
    generating at least one new available voice command based on said at least one new item of clinical data;
    incorporating the at least one new available voice command into the subset of available voice commands;
    receiving a spoken command from a user via an audio input device;
    comparing the spoken command with the subset of available voice commands; and
    executing a function of the display associated with said spoken command if said spoken command corresponds to the subset of available voice commands.

2. The method of claim 1, wherein a particular control is associated with at least one spoken command.

3. The method of claim 2, wherein the particular control is associated with at least two different spoken commands.

4. The method of claim 1, wherein a particular spoken command is a macro voice command for controlling more than one of said controls.

5. The method of claim 1, wherein a particular control comprises one of a button, a menu, a menu item, a list, a list box, a list item, a combo box, a radio button, a check box, a text area, a text pane, a scroll bar, a cursor, and a slider.

6. The method of claim 1, wherein a particular set of voice commands is for rearranging at least one of said windows in said display area.

7. The method of claim 6, wherein said rearranging comprises one of moving, maximizing, minimizing, opening, and closing one of said windows in said display area.

8. The method of claim 1, wherein said plurality of controls is a first plurality of controls, and said plurality of controls further comprises a second plurality of controls that are displayed within said display area.

9. The method of claim 1, wherein a particular set of voice commands is for altering at least one of said windows in said display area, wherein said altering comprises at least one of zoom in, zoom out, pan left, pan right, pan up, pan down, increase resolution, and decrease resolution.

10. The method of claim 1, wherein said data displayed in said display area comprises a list of selectable names, wherein a particular voice command that selects a particular name comprises the particular name itself.

11. The method of claim 10, wherein said particular voice command that selects the particular name comprises only the particular name itself.

12. The method of claim 1, wherein each time new clinical data is removed in the display, the voice command database is updated to include some of the content removed from the display.

13. The method of claim 1, wherein the medical computer system is located in a sterile environment.

14. The method of claim 1, wherein a visual feedback is provided in the display upon receiving the spoken command.

15. The method of claim 1, wherein an audio feedback is provided to a user upon successfully executing the spoken command.

16. The method of claim 15, wherein a separate audio feedback is provided to the user when the spoken command is unsuccessfully executed.

17. The method of claim 1, wherein the spoken command is customizable by a user.

18. The method of claim 1, wherein the clinical data is provided to the at least one clinical data database from at least two data sources.

19. The method of claim 1, wherein the method is used during a medical procedure.

20. The method of claim 1, wherein the at least two voice commands stored in the at least one voice command database are dynamic.

21. The method of claim 1, wherein the subset includes at least two voice commands.

22. The method of claim 1, wherein the first set of clinical data displayed is based upon an identification of a user.

23. The method of claim 1,
    wherein the step of comparing the spoken command with a subset of available voice commands includes converting the spoken command into a spoken text string and comparing the spoken text string to a plurality of text strings in the voice command database.

24. The method of claim 23, wherein if the spoken text string matches one of the plurality of text strings in the voice command database, the method includes the step of returning a token corresponding to the spoken text string and comparing the token against a second database to determine if the second database has a matching function to the token.

25. The method of claim 24, wherein if the second database has a matching function to the received token, executing the function associated with said spoken command to control at least one of said controls in the display.

26. The method of claim 25, wherein the second database includes multiple dashboard functions for each token.

27. A medical computer system comprising:
    at least one voice command database for storing at least two voice commands;
    at least one clinical data database for storing clinical data,
    a display, including a display area comprising a plurality of windows, the display having a plurality of controls for performing a plurality of functions and the display displaying some of the clinical data stored in the at least one clinical data database in the plurality of windows in the display area;

software executing on the computer system, the software executing on the computer system generating a subset of available voice commands based upon the data displayed in the plurality of windows displayed in the display area from a set of voice commands stored in at least one voice command database, the subset of available voice commands having fewer voice commands than the set of voice commands, the software executing on the computer system receiving at least one new item of clinical data, displaying said at least one new item of clinical data in the first set windows, generating at least one new available voice command based on said at least one new item of clinical data and incorporating the at least one new available voice command into the subset of available voice commands; and an audio input device, the audio input device able to receive a spoken command, such that upon receiving the spoken command, the software executing on the computer system compares the spoken command with the subset of available voice commands and executes a function associated with said spoken command if said spoken command corresponds to the subset of available voice commands.

28. The medical computer system of claim 27, wherein upon receiving the spoken command, the software executing on the computer converts the spoken command into a spoken text string and compares the spoken text string to a plurality of text strings in the voice command database.

29. The medical computer system of claim 28, wherein if the spoken text string matches one of the plurality of text strings in the voice command database, the method includes the step of returning a token corresponding to the spoken text string and comparing the token against a second database to determine if the second database has a matching function to the token.

30. The medical computer system of claim 29, wherein if the second database has a matching function to the received token, the method then executes the function associated with said spoken command to control at least one of said controls in the display.

31. The medical computer system of claim 30, wherein the second database controls multiple dashboard functions for each token.

32. The medical computer system of claim 27, wherein the token returned from the at least one voice command database corresponds to at least two different text strings.

33. The medical computer system of claim 27, wherein a particular control is associated with the spoken voice command.

34. The medical computer system of claim 27, wherein the software executing on the computer system includes software for speech recognition and software for interacting with the at least one voice command database and the at least one clinical data database.

35. The medical system of claim 27, wherein the subset includes at least two voice commands.

36. The medical computer system of claim 27, wherein the clinical data displayed in the display area is based upon the location of the user.

37. The medical computer system of claim 27, wherein the software executing on the computer system converts the spoken command into a spoken text string, compares the spoken text string to a plurality of text strings in the voice command database, and updates the subset of available voice commands with the spoken command.

* * * * *